United States Patent
Morley et al.

(10) Patent No.: US 8,906,622 B2
(45) Date of Patent: *Dec. 9, 2014

(54) METHOD OF AMPLIFICATION

(75) Inventors: Alexander Alan Morley, Adelaide (AU); Michael Julian Brisco, Campbelltown (AU)

(73) Assignee: Monoquant Pty Ltd, Adelaide (AU)

( * ) Notice: Subject to any disclaimer, the term of this patent is extended or adjusted under 35 U.S.C. 154(b) by 117 days.

This patent is subject to a terminal disclaimer.

(21) Appl. No.: 12/816,185

(22) Filed: Jun. 15, 2010

(65) Prior Publication Data

US 2010/0304444 A1    Dec. 2, 2010

Related U.S. Application Data

(63) Continuation of application No. PCT/AU2010/000680, filed on Jun. 2, 2010.

(60) Provisional application No. 61/217,707, filed on Jun. 2, 2009.

(51) Int. Cl.
*C12Q 1/68* (2006.01)

(52) U.S. Cl.
CPC ..................................... *C12Q 1/686* (2013.01)
USPC ......................................................... 435/6.12

(58) Field of Classification Search
None
See application file for complete search history.

(56) References Cited

U.S. PATENT DOCUMENTS

| | | | |
|---|---|---|---|
| 5,314,809 A | 5/1994 | Erlich et al. | |
| 5,340,728 A | 8/1994 | Grosz et al. | |
| 5,527,673 A * | 6/1996 | Reinhartz et al. | 435/6.19 |
| 5,556,773 A | 9/1996 | Yourno | |
| 7,273,730 B2 | 9/2007 | Du Breuil Lastrucci | |
| 7,329,493 B2 * | 2/2008 | Chou et al. | 435/6.15 |
| 2004/0072176 A1 * | 4/2004 | Lee et al. | 435/6 |
| 2006/0177844 A1 | 8/2006 | Ching et al. | |
| 2007/0281317 A1 * | 12/2007 | Becker et al. | 435/6 |

FOREIGN PATENT DOCUMENTS

| | | |
|---|---|---|
| CN | 1858219 | 11/2006 |
| CN | 1858219 A | 11/2006 |
| WO | WO 03/100019 | 12/2003 |
| WO | WO 2005/083114 | 9/2005 |

OTHER PUBLICATIONS

Smit et al. Journal of Virology (2004) 78(18): 10133-10148.*
Cheng et al. "Effective amplification of long targets from cloned inserts and human genomic DNA." Proc Natl Acad Sci. 91:5695-5699 (1994).
Fire et al. "Production of antisense RNA leads to effective and specific inhibition of gene expression in *C. elegains* muscle." Development. 113(2):503-514 (1991).
International Search Report for International Application No. PCT/AU2010/000680 dated Jul. 26, 2010.
Kemp et al. Simplified colorimetric analysis of polymerase chain reactions: detection of HIV sequences in AIDS. Gene. 94:223-228 (1990).
Sambrook and Russell. (2001) Molecular Cloning: A Laboratory Manual, 3$^{rd}$ Ed. Cold Spring Harbor, N.W.: Cold Spring Harbor Laboratory Press. Chapter 8: In vitro Amplification of DNA by the Polymerase Chain Reaction, table of contents only—1 page.
Borer, Philip N. et al., "Stability of Ribonucleic acid Double-stranded Helices" J. Mol. Biol., 1974, pp. 843-853, vol. 86.
Brisco, Michael J., et al., "Antisense PCR: A simple and robust method for performing nested single-tube PCR" Analytical Biochemistry, 2011, pp. 176-182, vol. 409.
Bustin, Stephen A. et al., "The MIQE Guidelines: Minimum Information for Publication of Quantitative Real-Time PCR Experiments" Clinical Chemistry, 2009, pp. 611-622, vol. 55, No. 4.
Cheng, Suzanne et al., "Effective amplification of long targets from cloned inserts and human genomic DNA" Proc. Natl. Acad. Sci., Jun. 1994, pp. 5695-5699, vol. 91.
Kemp, David J. et al., "Simplified colorimetric analysis of polymerase chain reaction: detection of HIV sequences in AIDS patients" Gene, 1990, pp. 223-228, vol. 94.
Sambrook, Joseph et al., "Molecular Cloning—A Laboratory Manual" Cold Spring Harbor Laboratory Press, 2001, vol. 2, Third Edition—Chapter 8 "In Vitro Amplification of DNA by the Polymerase Chain Reaction".
Santalucia Jr., John "A unified view of polymer, dumbbell, and oligonucleutide DNA nearest-neighbor thermodynamics" Proc. Natl. Acad. Sci., Feb. 1998, pp. 1460-1465, vol. 95.

* cited by examiner

*Primary Examiner* — Angela M Bertagna
(74) *Attorney, Agent, or Firm* — Knobbe Martens Olson & Bear LLP

(57) ABSTRACT

The present invention relates generally to a method of amplifying a nucleic acid region of interest and, more particularly, to a method of amplifying a nucleic acid region of interest via a nested single tube PCR. The method is designed to provide a means to selectively inactivate the functionality of the outer primer or primers and to maintain amplification efficiency throughout the reaction. The development of a means to achieve efficient amplification by the outer primer followed by efficient amplification with the inner primers, in the context of a single tube nested PCR, is useful in a range of applications including, but not limited to, the diagnosis and/or monitoring of disease conditions which are characterized by specific gene sequences and the characterization or analysis of specific gene regions of interest. Still further, the method enables quantification to be performed and not just simple detection.

19 Claims, 10 Drawing Sheets

FIGURE 4 (1/2)
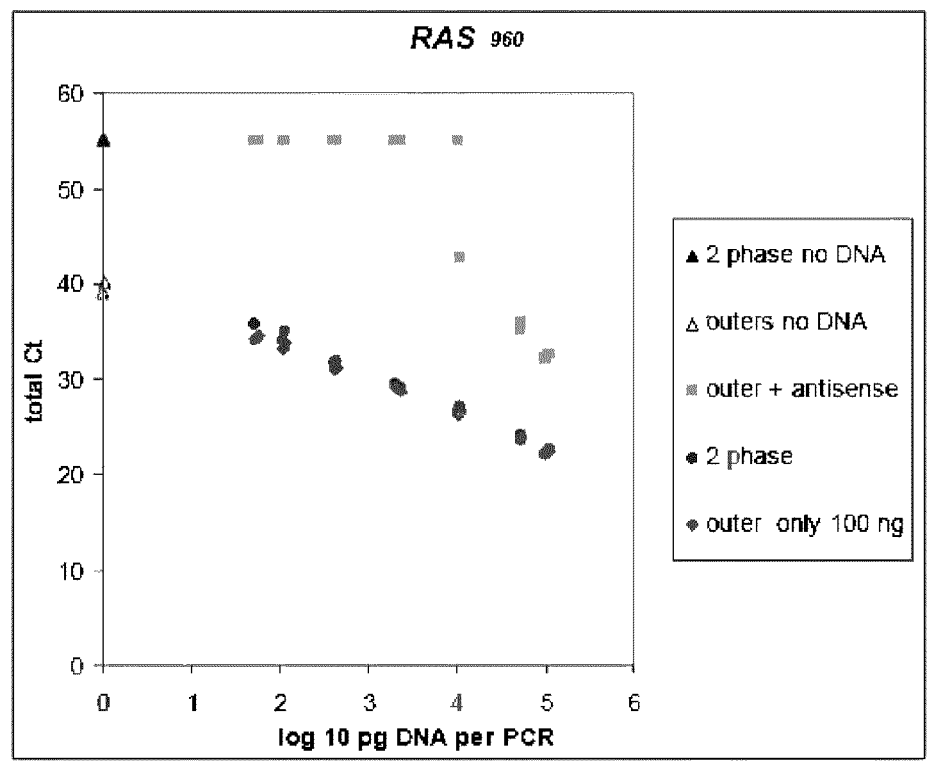
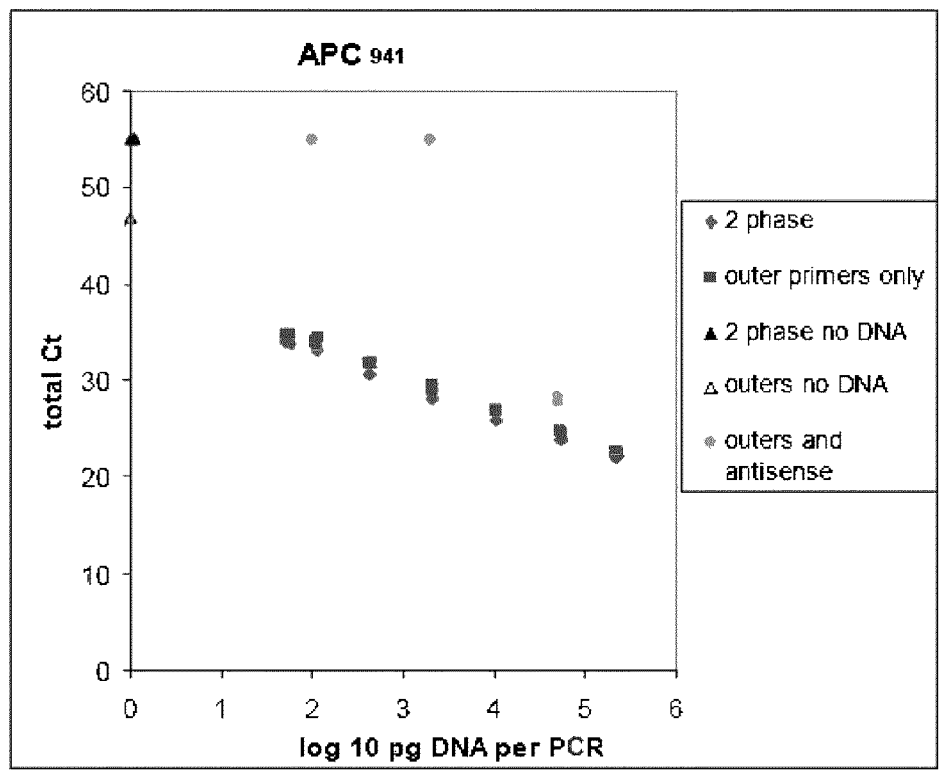

FIGURE 4 (2/2)
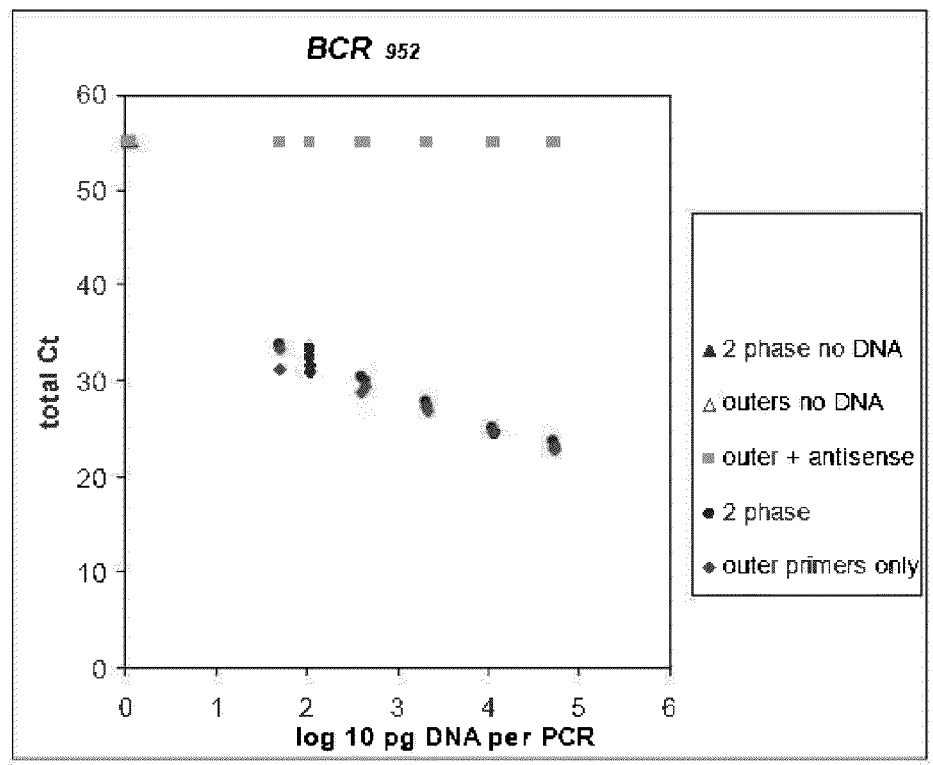
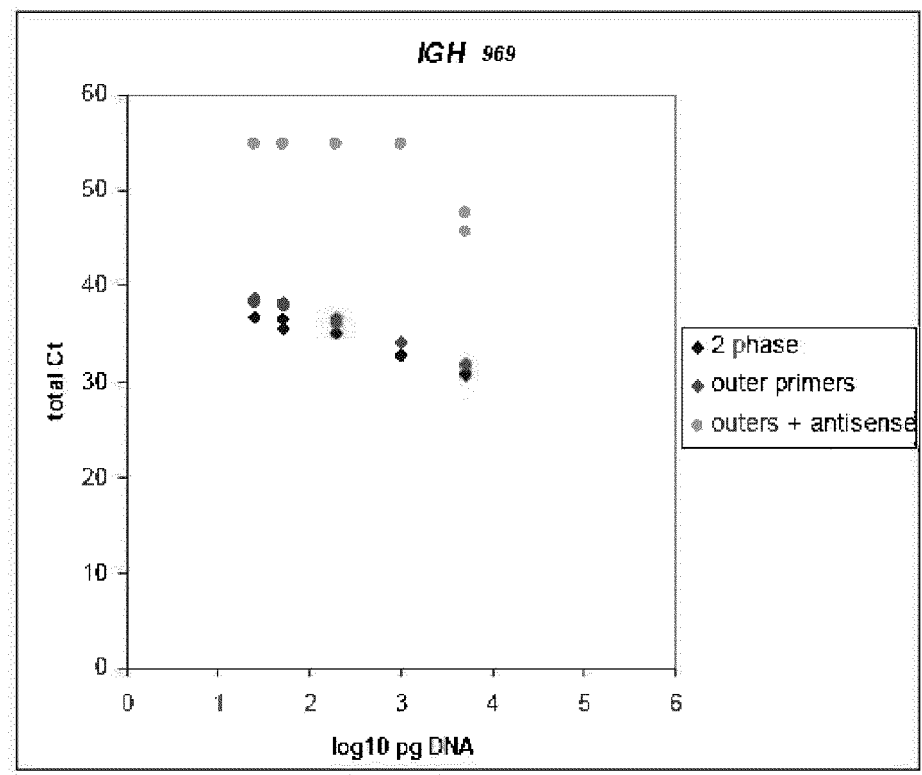

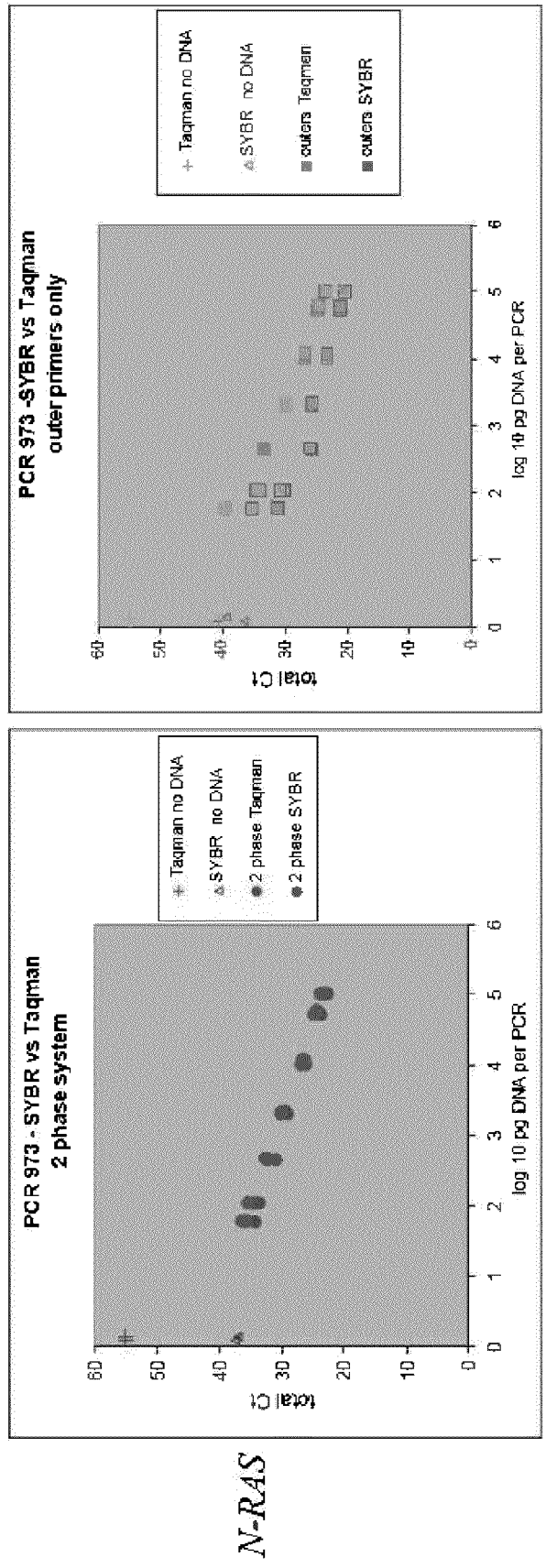
FIGURE 7 (1/3)

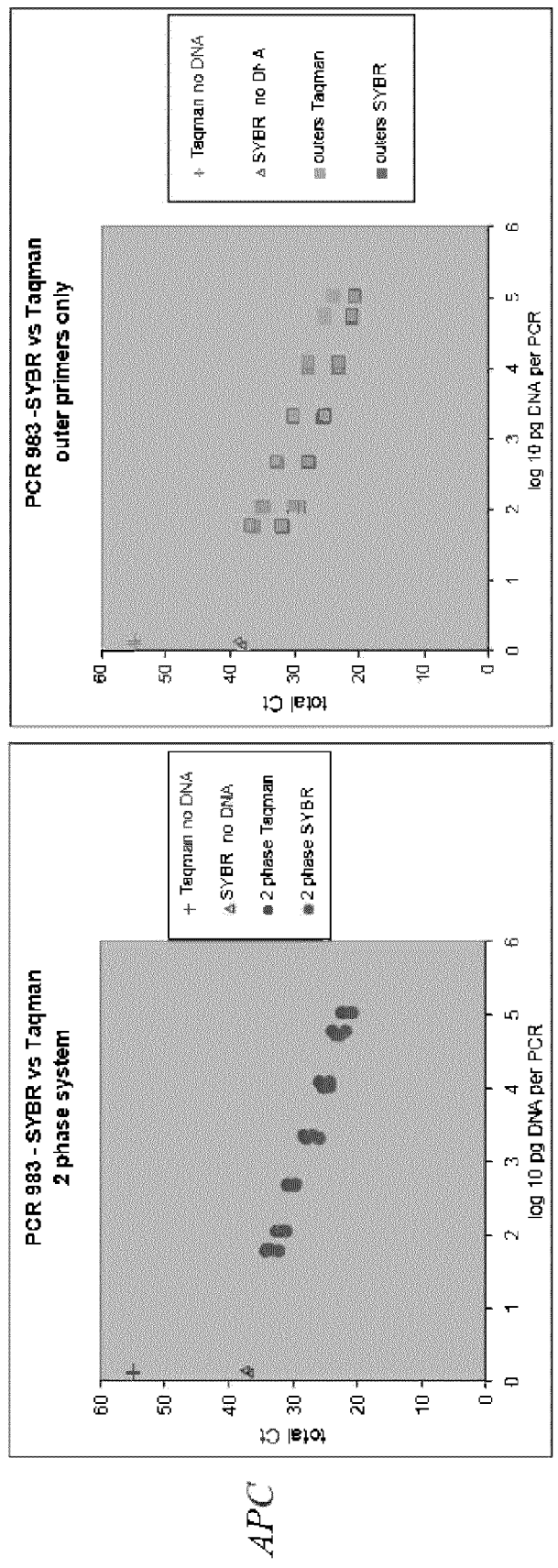
FIGURE 7 (2/3)

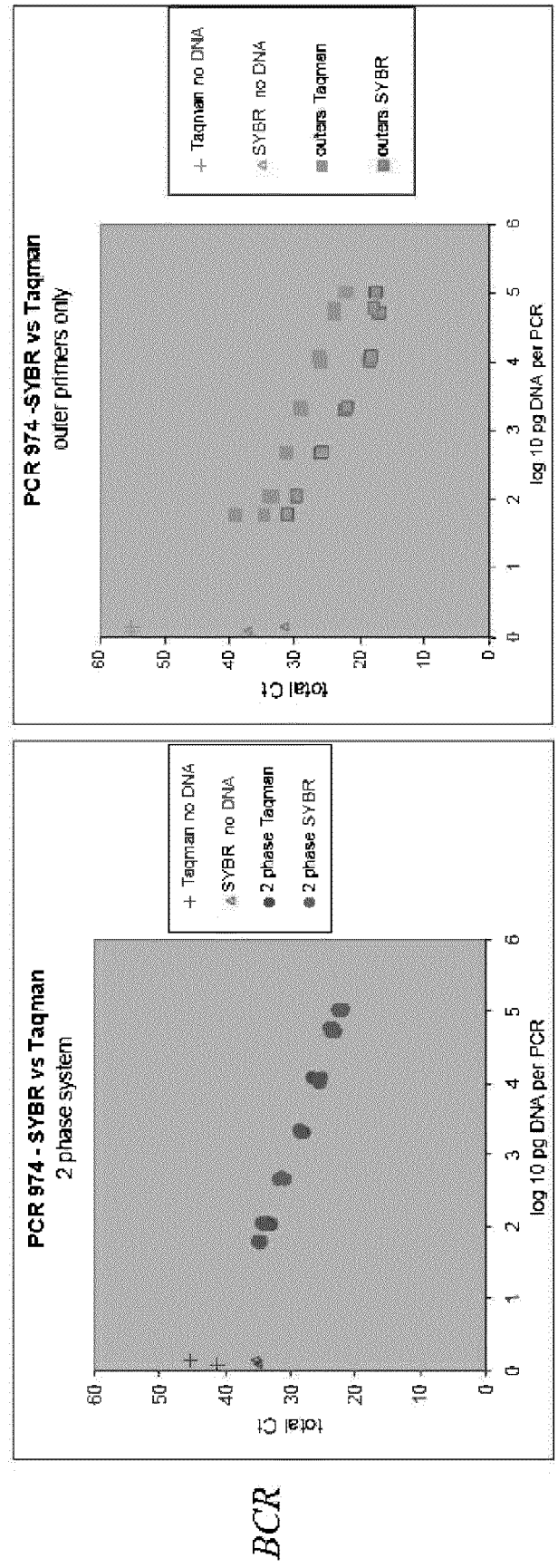
FIGURE 7 (3/3)

METHOD OF AMPLIFICATION

CROSS-REFERENCE TO RELATED APPLICATIONS

The present application is a continuation of International Patent Application No. PCT/AU2010/000680, filed Jun. 2, 2010, by MORLEY et al., entitled "A METHOD OF AMPLIFICATION," which claims priority to U.S. Provisional Application Ser. No. 61/217,707, filed on Jun. 2, 2009, by Morley, et al. and entitled "A METHOD OF AMPLIFICATION," which are hereby expressly incorporated by reference in their entireties.

BACKGROUND OF THE INVENTION

1. Field of the Invention

The present invention relates generally to a method of amplifying a nucleic acid region of interest and, more particularly, to a method of amplifying a nucleic acid region of interest via a nested single tube PCR. The method of the invention is designed to provide a means to selectively inactivate the functionality of the outer primer or primers and to maintain amplification efficiency throughout the reaction. The development of a means to achieve efficient amplification by the outer primer followed by efficient amplification with the inner primers, in the context of a single tube nested PCR, is useful in a range of applications including, but not limited to, the diagnosis and/or monitoring of disease conditions which are characterized by specific gene sequences and the characterization or analysis of specific gene regions of interest. Still further, the method of the present invention enables quantification to be performed and not just simple detection.

2. Description of the Related Art

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

Bibliographic details of the publications referred to by author in this specification are collected alphabetically at the end of the description.

The polymerase chain reaction (PCR) is a technique which is utilised to amplify specific regions of a DNA strand. This may be a single gene, just a part of a gene or a non-coding sequence. Most PCR methods typically amplify DNA fragments of up to 10 kilo base pairs (kb), although some techniques allow for amplification of fragments up to 40 kb in size (Cheng et al., 1994, *Proc Natl Acad Sci.* 91:5695-5699).

PCR, as currently practiced, requires several basic components (Sambrook and Russel, 2001, *Molecular Cloning: A Laboratory Manual*, $3^{rd}$ Ed.). These components are:

a DNA template which contains the region of the DNA fragment to be amplified;

primers, which are complementary to the DNA regions at the 5' and 3' ends of the DNA region that is to be amplified;

a DNA polymerase (e.g. Taq polymerase or another thermostable DNA polymerase with a temperature optimum at around 70° C.), used to synthesize a DNA copy of the region to be amplified; and Deoxynucleotide triphosphates (dNTPs) from which the DNA polymerase builds the new DNA.

PCR is carried out in small reaction tubes (0.2-0.5 ml volumes), containing a reaction volume typically of 15-100 µl, which are inserted into a thermal cycler. This machine heats and cools the reaction tubes within it to the precise temperature required for each step of the reaction. Most thermal cyclers comprise heated lids to prevent condensation on the inside of the reaction tube caps. Alternatively, a layer of oil may be placed on the reaction mixture to prevent evaporation.

Accordingly, PCR is a method that allows exponential amplification of DNA sequences within a longer DNA molecule. The reaction involves a number of cycles of amplification, and in each cycle the template for each molecular reaction is either a strand of the initial DNA in the sample or a strand of DNA synthesised in a preceding cycle. Each PCR cycle involves the following steps denaturation by heat to separate the 2 strands of the DNA duplex hybridization of the upstream and downstream primers to their complementary sequences extension of the primers by the DNA polymerase to produce a complementary copy of the template sequence Typically the PCR reagents and conditions are chosen so that denaturation, hybridization and extension occur at close to maximum efficiency and as a result the amount of the desired sequence increases with each cycle by a factor of close to 2. Substantial amplification occurs by the end of the PCR eg a 30 cycle PCR will result in amplification of the original template by a factor of almost $2^{30}$ (1,000,000,000). This degree of amplification facilitates detection and analysis of the amplified product.

After a number of cycles of amplification, the PCR may be terminated and the product analysed in various ways, most commonly by gel electrophoresis. When the PCR is carried out to a finite endpoint, the amount of amplified product is usually not closely related to the amount of input target DNA, and this type of PCR is rather a qualitative tool for detecting the presence or absence of a particular DNA and/or for providing sufficient target DNA for further analysis.

In order to measure messenger RNA (mRNA), the method uses reverse transcriptase to initially convert mRNA into complementary DNA (cDNA) which is then amplified by PCR and analyzed by agarose gel electrophoresis. Reverse transcription followed by end-point PCR is similarly essentially a qualitative technique.

In order to provide quantification capability, real-time PCR was developed. This procedure follows the general pattern of PCR, but the amplified DNA is quantified during each cycle. Two common methods of quantification are the use of fluorescent dyes that intercalate with double-stranded DNA and modified DNA oligonucleotide primers or probes the fluorescence of which changes during one of the steps of the PCR. Frequently, real-time polymerase chain reaction is combined with reverse transcriptase polymerase chain reaction to quantify low abundance messenger RNA (mRNA), enabling a researcher to quantify relative gene expression at a particular time or in a particular cell or tissue type.

(i) Real-Time PCR Using Dyes Binding to Double-Stranded DNA

A DNA-binding dye, such as Sybr Green, binds to all double-stranded (ds)DNA in a PCR reaction, causing increased fluorescence of the dye. An increase in DNA product during PCR therefore leads to an increase in fluorescence intensity which is measured at each cycle, thus allowing DNA concentrations to be quantified.

(ii) Fluorescent Reporter Sequence Methods

A number of different methods using fluorescent reporter primers or probes have been developed and they tend to be more accurate and reliable than use of DNA binding dyes. They use one or more DNA primers or probes to quantify only the DNA to which the primer or probe hybridises. Use of a reporter probe, such as a Taqman probe, significantly increases specificity and may allow quantification even in the presence of some non-specific DNA amplification. Use of sequence-specific primers or probes allows for multiplexing—assaying for several different amplified products in the same reaction by using specific sequences or probes with different-coloured labels, provided that all targets are amplified with similar efficiency.

In terms of quantification, relative concentrations of DNA present during the exponential phase of the reaction are determined by plotting fluorescence against cycle number on a logarithmic scale. A threshold for increase of fluorescence above background or decrease below background (depending on the precise method) is determined. The cycle at which the fluorescence from a sample crosses the threshold is called the cycle threshold, $C_t$.

The amount of target DNA is then determined by comparing the test results to the results produced by one or more standards. When the target DNA is genomic DNA, then a series of standards, usually 10 fold dilutions of a known amount of the target DNA, are commonly used. When the target DNA is cDNA, then one or more internal standards of the cDNA of another gene are commonly used.

A variation of traditional PCR, designed to increase the specificity of the PCR amplification, is the nested PCR reaction. In this amplification reaction, two sets of primers are used in two successive reactions. In the first, one pair of primers is used to generate DNA products, which may also contain products amplified from non-target areas. The products from the first PCR are then used to start a second, using one ('hemi-nesting') or two different primers whose binding sites are located (nested) within the first set. The specificity of all of the primers is combined, usually leading to a single product.

Nested PCR is conventionally performed by carrying out an initial PCR in one reaction tube, transferring an aliquot of the amplified products into a second reaction tube, and then carrying out a second PCR. This procedure has two disadvantages. It is more complex than a single PCR and, more importantly, it carries the risk of contaminating the environment with the amplified products of the first PCR, which may lead to contamination of subsequent experimental procedures. For this reason, several methods have been developed for carrying out the successive PCRs in the one reaction tube.

Carrying out two rounds of PCR in the one reaction tube involves adding the primers for the two rounds into the initial reaction mixture. The methods that have then been used for producing two sequential rounds of PCR, the first using the outer pair of primers and the second using the inner pair, include:

using different annealing temperatures for the two rounds of PCR (Kemp et al., *Gene* 1990, 94:223-228, Erlich et al. U.S. Pat. No. 5,314,809), decreasing the concentration of the primers for the first round PCR (Erlich et al. U.S. Pat. No. 5,314,809)

varying the annealing times for the two rounds of PCR Grosz et al U.S. Pat. No. 5,340,728)

modifying the structure of the primers for the second round of PCR and using two different annealing temperatures during this round. (Xu Dingbang Publication CN1858219).

using a low denaturation temperature for the second round PCR (Erlich et al U.S. Pat. No. 5,314,809)

using chemically modified primers for the first round PCR and an enzyme which would progressively destroy them (Du Breuil Lastrucci U.S. Pat. No. 7,273,730)

using an initial physical separation of the reagents for the first and second round PCRs (Yourno U.S. Pat. No. 5,556,773, Ching et al. United States Patent Application 20060177844).

The principle underlying all of these methods is to produce, at some point, a rapid or gradual inhibition of the activity of the primers for the first round PCR so that ongoing amplification depends progressively on the activity of the primers for the second round PCR. However, all of these methods have disadvantages, the nature of the disadvantage depending upon the method. Their robustness varies and the reaction conditions may need to be adjusted depending on the sequence of interest which is to be amplified. Amplification may be inefficient, in some cases throughout the first round PCR and in other cases during the transition from the first round to the second round PCR. As a consequence, some of the approaches are not widely used in practice, whereas others are used only for detection and not for quantification.

In work leading up to the present invention, a single tube nested PCR method has been developed which facilitates both specificity and efficiency by providing a mechanism to selectively inactivate the functionality of the outer primer once it is no longer required, thereby enabling efficient amplification using the outer primers followed by efficient amplification using the inner primer. This has therefore enabled the development of a PCR method which is sufficiently efficient to effect quantification, as well as detection, and which provides the unique advantages of a single tube nested PCR reaction.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

One aspect of the present invention is directed to a method of amplifying a nucleic acid region of interest, said method comprising:

(i) contacting a nucleic acid sample with:
(a) a first forward primer directed to said region of interest and a first reverse primer directed to said region of interest; and
(b) a second forward primer directed to said region of interest wherein said second forward primer is directed to a nucleic acid sequence located 3' to the sequence to which said first forward primer is directed and which second forward primer has a $T_m$ lower than the $T_m$ of said first forward primer; and
a second reverse primer directed to said region of interest wherein said second reverse primer is directed to a nucleic acid sequence located 5' to the sequence to which said first reverse primer is directed and which second reverse primer has a $T_m$ lower than the $T_m$ of said first reverse primer; and (c) one or more antisense oligonucleotides directed to said first primer, which antisense oligonucleotides have a $T_m$ lower than said first primer; and wherein the molecules of parts (b) and (c) can be added to the reaction before, during or after the amplification of step (ii) but before the amplification of step (iii).

(ii) amplifying the nucleic acid sample of step (i) at an annealing temperature which enables hybridization of said first primers but which does not enable hybridization of said second primers and said antisense oligonucleotides; and (iii) amplifying the nucleic acid sample of step (ii) at an annealing temperature which enables hybridization of said second primers and said antisense oligonucleotides.

In another aspect of the present invention is directed to a method of amplifying a DNA region of interest, said method comprising:

(i) contacting a DNA sample with:
(a) a first forward primer directed to said region of interest and a first reverse primer directed to said region of interest; and
(b) a second forward primer directed to said region of interest wherein said second forward primer is directed to a nucleic acid sequence located 3' to the sequence to which said first forward primer is directed and which second forward primer has a $T_m$ lower than the $T_m$ of said first forward primer; and
a second reverse primer directed to said region of interest wherein said second reverse primer is directed to a nucleic acid sequence located 5' to the sequence to which said first reverse primer is directed and which second reverse primer has a $T_m$ lower than the $T_m$ of said first reverse primer; and
(c) one or more antisense oligonucleotides directed to said first primer, which antisense oligonucleotides have a $T_m$ lower than said first primer; and
wherein the molecules of parts (b) and (c) can be added to the reaction before, during or after the amplification of step (ii) but before the amplification of step (iii), (ii) amplifying the DNA sample of step (i) at an annealing temperature which enables hybridization of said first primers but which does not enable hybridization of said second primers and said antisense oligonucleotides; and (iii) amplifying the DNA sample of step (ii) at an annealing temperature which enables hybridization of said second primers and said antisense oligonucleotides.

In yet another aspect of the present invention is directed to a method of amplifying a DNA region of interest, said method comprising:

(i) contacting a DNA sample with:
(a) a first forward primer directed to said region of interest and a first reverse primer directed to said region of interest; and
(b) a second forward primer directed to said region of interest wherein said second forward primer is directed to a nucleic acid sequence located 3' to the sequence to which said first forward primer is directed and which second forward primer has a $T_m$ lower than the $T_m$ of said first forward primer; and
a second reverse primer directed to said region of interest wherein said second reverse primer is directed to a nucleic acid sequence located 5' to the sequence to which said first reverse primer is directed and which second reverse primer has a $T_m$ lower than the $T_m$ of said first reverse primer; and
(c) one or more antisense oligonucleotides directed to said first primer, which antisense oligonucleotides have a $T_m$ lower than said first primers and one of which antisense oligonucleotide hybridizes to the 3' end of the primer and comprises a 5' nucleic acid tag sequence, the complementary nucleotide sequence of which tag is mismatched relative to the nucleotide sequence of the DNA region adjacent to the 5' end of the hybridization site of said primer wherein the molecules of parts (b) and (c) can be added to the reaction before, during or after the amplification of step (ii) but before the amplification of step (iii);

(ii) amplifying the DNA sample of step (i) at an annealing temperature which enables hybridization of said first primers but which does not enable hybridization of said second primers and said antisense oligonucleotides; and (iii) amplifying the DNA sample of step (ii) at an annealing temperature which enables hybridization of said second primers and said antisense oligonucleotides.

In still another aspect the present invention is directed to a method of amplifying a DNA region of interest, said method comprising:

(i) contacting a DNA sample with:
(a) a first forward primer directed to said region of interest and a first reverse primer directed to said region of interest; and
(b) a second forward primer directed to said region of interest wherein said second forward primer is directed to a nucleic acid sequence located 3' to the sequence to which said first forward primer is directed and which second forward primer has a $T_m$ lower than the $T_m$ of said first forward primer; and
a second reverse primer directed to said region of interest wherein said second reverse primer is directed to a nucleic acid sequence located 5' to the sequence to which said first reverse primer is directed and which second reverse primer has a $T_m$ lower than the $T_m$ of said first reverse primer; and
(c) one or more antisense oligonucleotides directed to said first primer, which antisense oligonucleotides have a $T_m$ lower than said first primers and one or more of which antisense oligonucleotides comprises a 3' end which cannot undergo normal extension wherein the molecules of parts (b) and (c) can be added to the reaction before, during or after the amplification of step (ii) but before the amplification of step (iii);

(ii) amplifying the DNA sample of step (i) at an annealing temperature which enables hybridization of said first primers but which does not enable hybridization of said second primers and said antisense oligonucleotides; and (iii) amplifying the DNA sample of step (ii) at an annealing temperature which enables hybridization of said second primers and said antisense oligonucleotides.

In yet still another aspect the present invention is directed to a method of amplifying a DNA region of interest, said method comprising:

(i) contacting a DNA sample with:
(a) a first forward primer directed to said region of interest and a first reverse primer directed to said region of interest; and
(b) a second forward primer directed to said region of interest wherein said second forward primer is directed to a nucleic acid sequence located 3' to the sequence to which said first forward primer is directed and which second forward primer has a $T_m$ lower than the $T_m$ of said first forward primer; and
a second reverse primer directed to said region of interest wherein said second reverse primer is directed to a nucleic acid sequence located 5' to the sequence to which said first reverse primer is directed and which second reverse primer has a $T_m$ lower than the $T_m$ of said first reverse primer; and (c) one or more antisense oligonucleotides directed to said first primer, which antisense oligonucleotides have a $T_m$ lower than said first primers and which antisense oligonucleotides comprise:

a 5' nucleic acid tag sequence on the antisense oligonucleotide which hybridizes to the 3' end of the primer, the complementary nucleotide sequence of which tag is mismatched relative to the nucleotide sequence of the DNA region adjacent to the 5' end of the hybridization site of said primer; and a 3' end which cannot undergo normal extension wherein the molecules of parts (b) and (c) can be added to the reaction before, during or after the amplification of step (ii) but before the amplification of step (iii);

(ii) amplifying the DNA sample of step (i) at an annealing temperature which enables hybridization of said first primers but which does not enable hybridization of said second primers and said antisense oligonucleotides; and (iii) amplifying the DNA sample of step (ii) at an annealing temperature which enables hybridization of said second primers and said antisense oligonucleotides.

According to this embodiment there is provided a method of amplifying a DNA region of interest, said method comprising:

(i) contacting a DNA sample with:

(a) a first forward primer directed to said region of interest and a first reverse primer directed to said region of interest; and (b) a second forward primer directed to said region of interest wherein said second forward primer is directed to a nucleic acid sequence located 3' to the sequence to which said first forward primer is directed and which second forward primer has a $T_m$ which is 5, 6, 7, 8, 9, 10, 11, 12, 13, 14, 15, 16, 17, 18, 19 or 20° C. lower than the $T_m$ of said first forward primer; and a second reverse primer directed to said region of interest wherein said second reverse primer is directed to a nucleic acid sequence located 5' to the sequence to which said first reverse primer is directed and which second reverse primer has a $T_m$ which is 5, 6, 7, 8, 9, 10, 11, 12, 13, 14, 15, 16, 17, 18, 19 or 20° C. lower than the $T_m$ of said first reverse primer; and (c) one or more antisense oligonucleotides directed to said first primer, which antisense oligonucleotides have a $T_m$ which is 10, 11, 12, 13, 14, 15, 16, 17, 18, 19, 20, 21, 22, 23, 24, 25, 26, 27, 28, 29 or 30° C. lower than said first primers and which antisense oligonucleotides comprise:

a 5' nucleic acid tag sequence on the antisense oligonucleotide which hybridizes to the 3' end of the primer, the complementary nucleotide sequence of which tag is mismatched relative to the nucleotide sequence of the DNA region adjacent to the 5' end of the hybridization site of said primer; and a 3' end which cannot undergo normal extension wherein the molecules of parts (b) and (c) can be added to the reaction before, during or after the amplification of step (ii) but before the amplification of step (iii); and (ii) amplifying the DNA sample of step (i) at an annealing temperature which enables hybridization of said first primers but which does not enable hybridization of said second primers and said antisense oligonucleotides; and (iii) amplifying the DNA sample of step (ii) at an annealing temperature which enables hybridization of said second primers and said antisense oligonucleotides.

A further embodiment of the present invention is directed to a method of amplifying a DNA region of interest, said method comprising:

(i) contacting a DNA sample with:

(a) a first forward primer directed to said region of interest and a first reverse primer directed to said region of interest; and (b) a second forward primer directed to said region of interest wherein said second forward primer is directed to a nucleic acid sequence located 3' to the sequence to which said first forward primer is directed and which second forward primer has a $T_m$ lower than the $T_m$ of said first forward primer; and a second reverse primer directed to said region of interest wherein said second reverse primer is directed to a nucleic acid sequence located 5' to the sequence to which said first reverse primer is directed and which second reverse primer has a $T_m$ lower than the $T_m$ of said first reverse primer; and (c) a third forward primer directed to said region of interest wherein said third forward primer is directed to a DNA sequence located 3' to the sequence to which said second forward primer is directed and said third forward primer has a $T_m$ lower than the $T_m$ of said second forward primer; and a third reverse primer directed to said region of interest wherein said third reverse primer is directed to a DNA sequence located 5' to the sequence to which said second reverse primer is directed and wherein said third reverse primer has a $T_m$ value lower than the $T_m$ values of said second reverse primer; and (d) one or more antisense oligonucleotides directed to said first primer, which antisense oligonucleotides have a $T_m$ lower than said first primers and one or more antisense oligonucleotides directed to the said second primer, each of which antisense oligonucleotides has a $T_m$ lower than said second primers wherein the molecules of parts (b), (c) and (d) can be added to the reaction before, during or after the amplification of step (ii) but before the amplification of step (iii);

(ii) amplifying the DNA sample of step (i) at an annealing temperature which enables hybridization of said first primers but which does not enable hybridization of said second primers and third primers and said antisense oligonucleotides; and (iii) amplifying the DNA sample of step (ii) at an annealing temperature which enables hybridization of said second primers and said antisense oligonucleotides directed to said first primers but which does not enable hybridization of said third primers and said antisense oligonucleotides directed to said second primers;

(iv) amplifying the DNA sample of step (iii) at an annealing temperature which enables hybridization of said third primers and said antisense oligonucleotides directed to the said second primers.

During the first phase of the PCR, the annealing temperature is sufficiently high so that the only hybridization that occurs is between the outer primers and the template and efficient amplification therefore occurs. During the second phase of the PCR, the annealing temperature is sufficiently low to enable 2 mechanisms to occur.

the antisense oligonucleotides hybridize to the outer primers which extend along them and thus become unable to cause extension along the PCR template, even if they do subsequently hybridize to it.

the inner primers hybridize and extend so that efficient PCR amplification continues.

Figure 1:
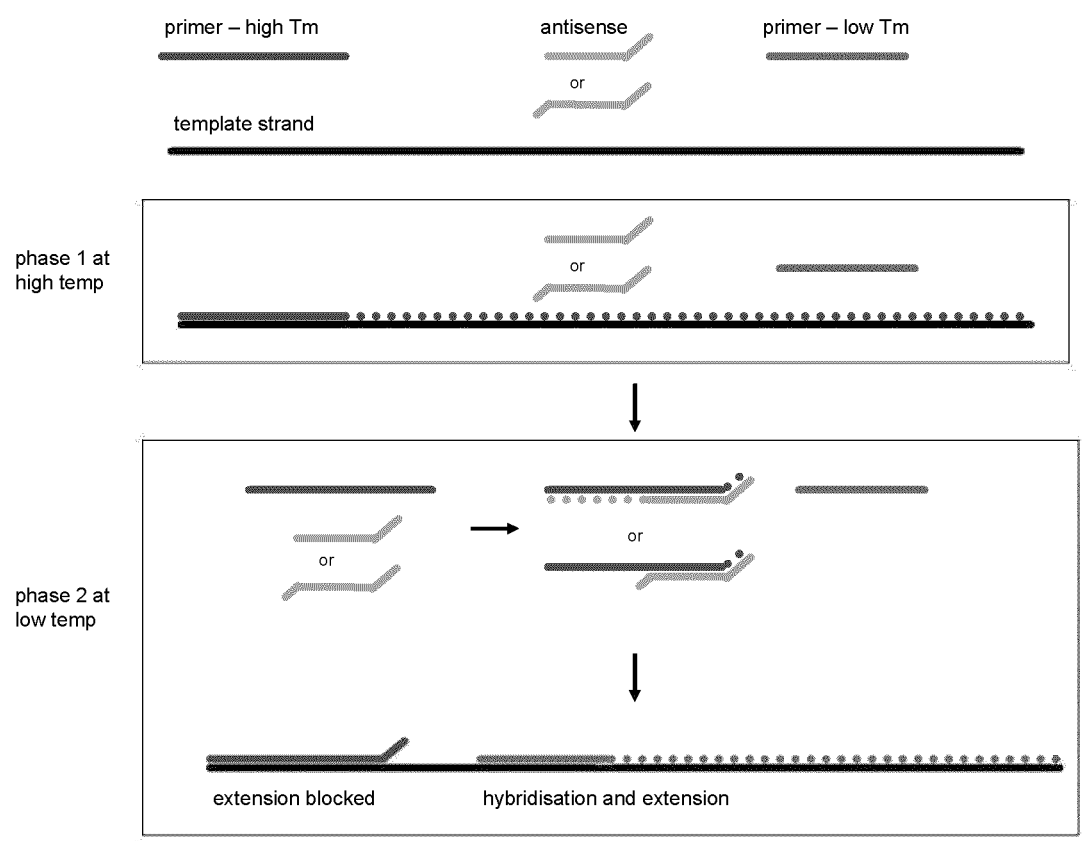
FIG. 1 is a schematic representation of the Strategy of the 2 phase nested single-tube quantitative PCR. The reaction contains outer primers which have a high Tm, antisense oligonucleotides which have a Tm which is sufficiently low to prevent binding to the outer primers at the high temperature of the first phase but which is sufficiently high to enable binding at the low temperature of the second phase, and inner primers which also have a Tm which is sufficiently low to prevent binding to the template strand at the high temperature of the first phase but which is sufficiently high to enable binding at the lower temperature of the second phase. A number of designs of the antisense oligonucleotides are possible, and two are shown in the figure. The most favoured design involves (a) a small extension at the 5' end which is designed so that a mismatch to the template strand will be produced if the outer primer binds to the antisense oligonucleotide and extends, and (b) a small extension at the 3' end which results in a mismatch which prevents extension of the antisense oligonucleotide along the full length of the outer primer.
Figure 2:
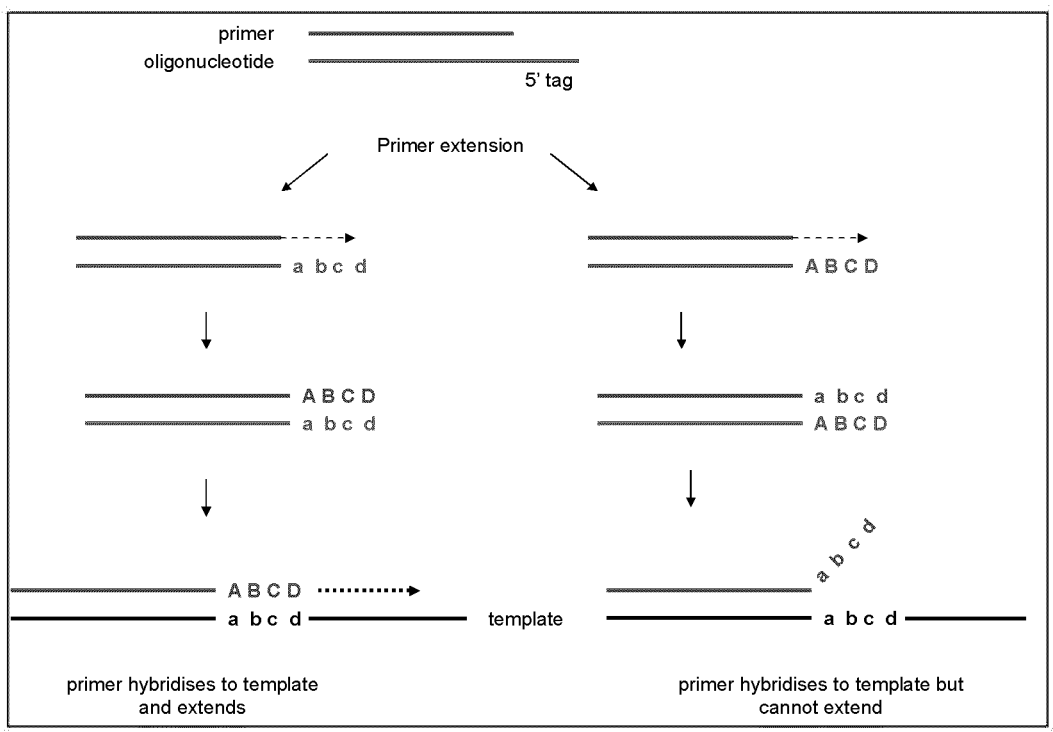

FIG. 2 is a schematic representation of the functional effect resulting from the sequence of the 5' tag on the antisense oligonucleotide. Different nucleotide bases are conceptually represented as A, B, C, D and the complementary bases as a, b, c, d. If the tag sequence is abcd in the 3' to 5' direction then sequence of the primer extension will be ABCD in the 5' to 3' direction and the extended primer will match perfectly to its template, extend further and amplify efficiently. Any other sequence of the oligonucleotide tag will result in partial or complete mismatch between the extended primer and the template strand and partial or complete inactivation of the primer. The simplest strategy for producing a complete mismatch is to use the sequence ABCD for the tag sequence, which is complementary to the template sequence abcd (3' to 5') and which is also the sequence (5' to 3') produced by extension of the native primer on its template.

Figure 3:
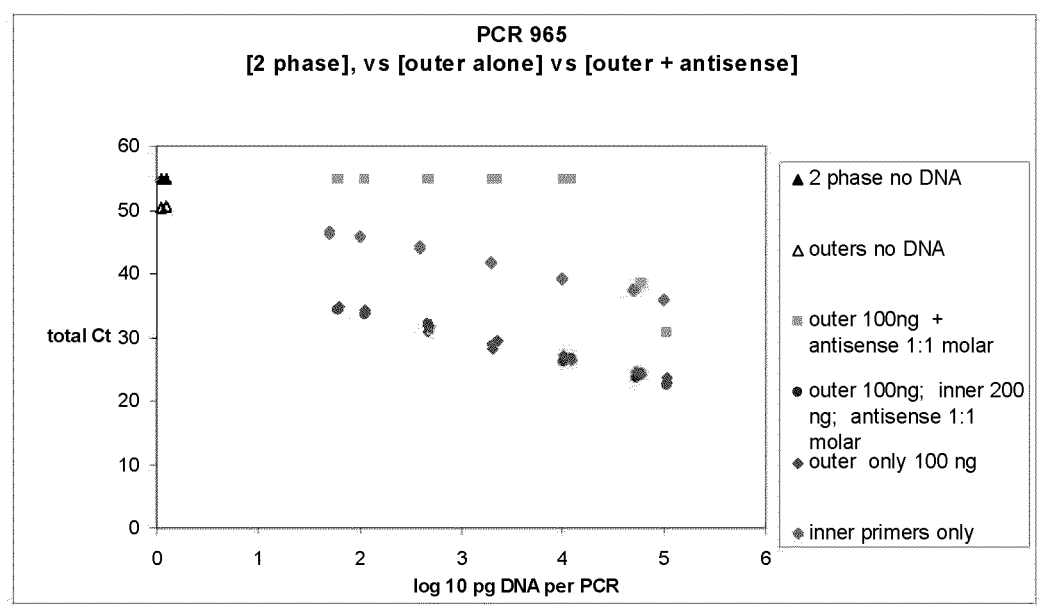

FIG. 3 is a graphical representation of the CT values when the N-RAS gene was quantified in masses of DNA ranging from 100 ng to 50 pg, and the annealing temperature for the PCR is 72° C. for the first 15 cycles and 58° C. for the remaining cycles. The points shown in red are the results of a standard PCR using the "outer" primers. The points shown in blue are the results of the two-phase one-tube protocol in which the PCR contains the outer primers, the antisense oligonucleotide to the outer primers, and the inner primers. It can be seen that the two-phase one-tube protocol gives identical results to the standard PCR, indicating that it has optimal efficiency. During the first 15 cycles, amplification is driven at optimal efficiency by the outer primers as neither the antisense oligonucleotide nor the inner primers can anneal. During subsequent cycles the antisense oligonucleotide progressively inactivates the outer primers but the inner primers can anneal and produce amplification at optimal efficiency. The data in green are the results when the PCR only contains the outer primers and the antisense oligonucleotide. Ct values of 50 or more indicate no amplification and it can be seen that the outer primers are switched off progressively once the annealing temperature is 58° C. The points shown in violet are the Ct values for the inner primers alone. The Ct values are delayed approximately 15 cycles indicating that the inner primers do not anneal during the first 15 cycles. The open and closed triangles are results from control tubes containing no DNA.

FIG. 4 is a graphical representation of the analysis of performance of the 2 phase single-tube nested PCR system. Four genes were studied—N-RAS, APC, BCR, and a rearranged IGH gene, and a range of masses of DNA were used for amplification in order to produce a range of Ct values. Fifteen cycles were performed at 72° C., the remaining cycles at 58° C., and Ct was determined using a TAQMAN® probe. The blue symbols indicate conventional PCRs using the outer primers only; the red symbols indicate 2 phase PCRs containing the outer primers, the antisense oligonucleotides (which are directed against the outer primers), and the inner primers; and the green symbols indicate PCRs containing the outer primers and the antisense oligonucleotides. The 2 phase system gives the same Ct results as a conventional PCR but amplification during the 58° C. second phase is mediated by the inner primers, as evidenced by the inhibitory effect of the antisense oligonucleotide when the inner primers are absent. A Ct value of 55 indicates a negative result.

The observation that the method enabled the development of an efficient nested single tube PCR for all four genes and using the same experimental conditions attests to the robustness of the method.

Figure 5:
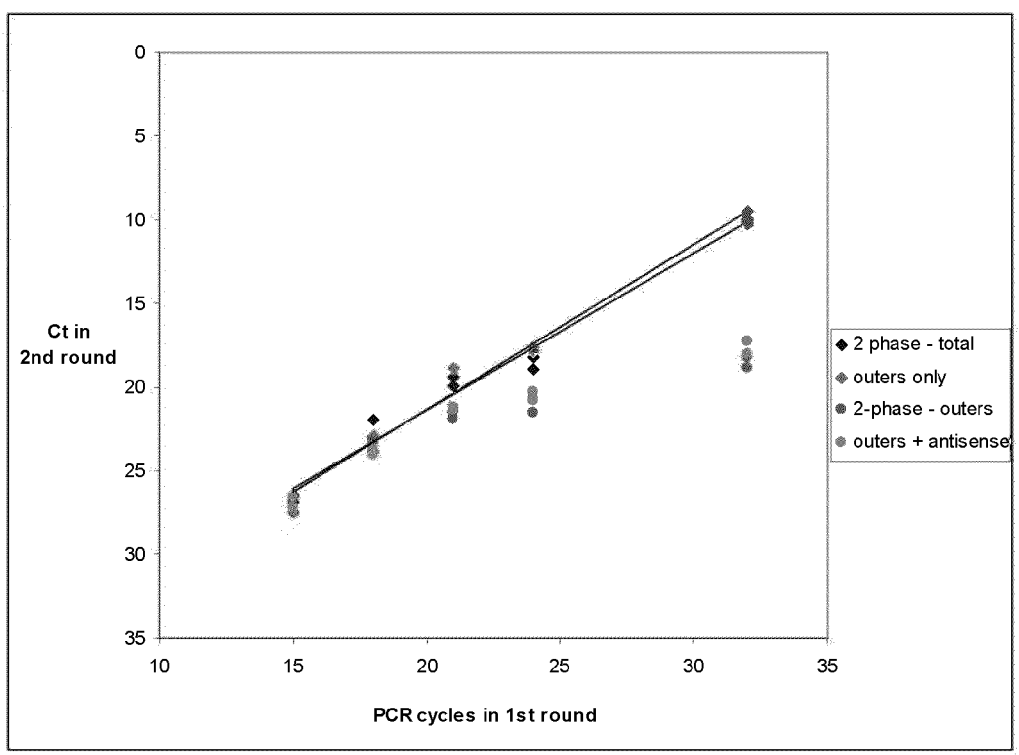

FIG. 5 is a graphical representation of the dynamics of the two phase nested PCR system and illustrates the progressive inhibitory effect of the antisense oligonucleotides on the activity of the outer primers. PCR amplification was performed using either the 2 phase system, the outer primers only, or the outer primers in the presence of the antisense oligonucleotides. After either 15, 18, 21, 24 or 32 cycles the PCR was stopped and an aliquot was assayed in a second round PCR in order to measure the amplification of both long and short amplicons in the two phase PCR or the long amplicons in the other 2 PCRs in which the inner primers were absent and amplification was only due to the outer primers. Note that the Ct values are shown inversely in order to illustrate the increasing amount of product generated with increasing cycles of the PCR. There is an exponential increase both in the total number of amplicons in the two phase PCR and in the number of long amplicons in the PCR in which only the long primers are present (the regression lines for both sets of data are shown). However, when antisense oligonucleotides are present, amplification of long amplicons gradually slows both in the two phase PCR and in the PCR in which the only primers present are the long primers.

Figure 6:
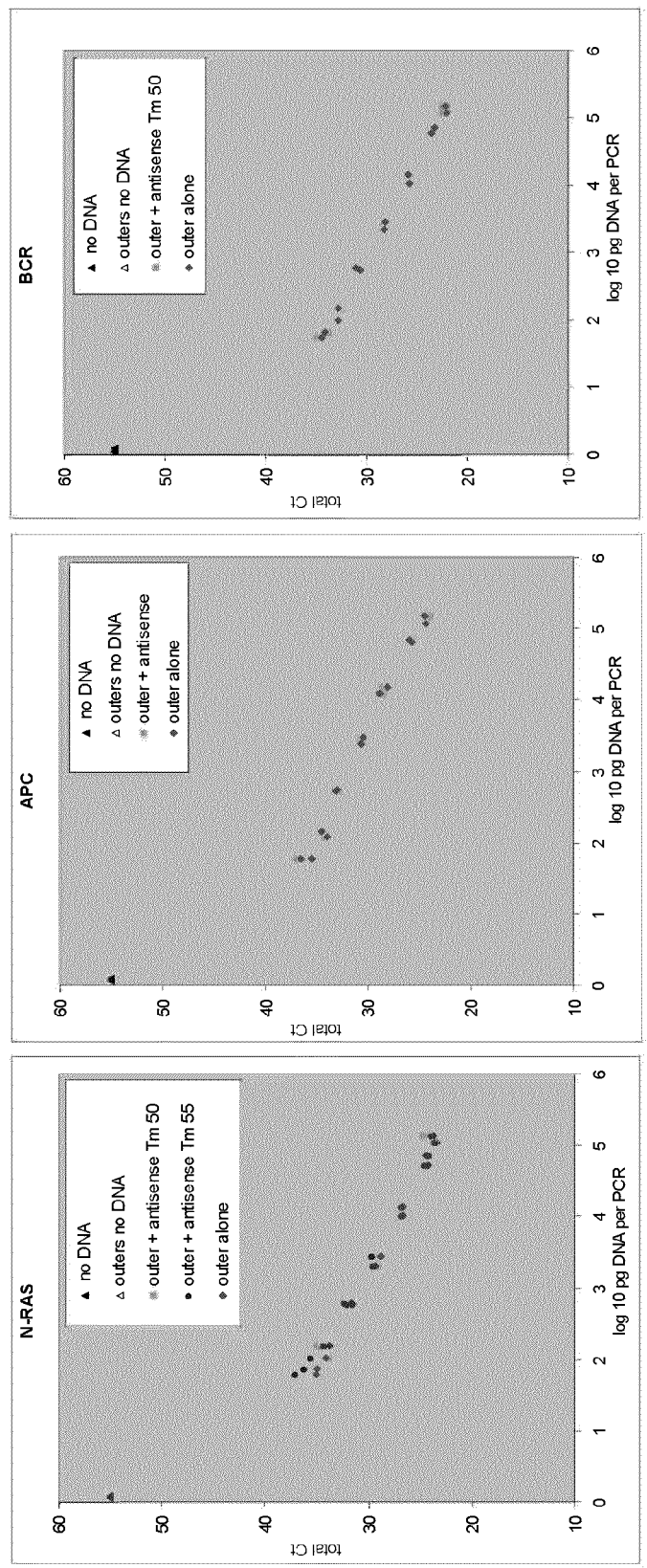

FIG. 6 is a graphical representation of the lack of inhibitory effect of antisense oligonucleotides on amplification by outer primers when annealing temperature is 72° C., as is the case in the first phase of the 2-phase nested PCR. Three genes, N-RAS, APC and BCR, were studied and the effects of 2 pairs of antisense oligonucleotides was somewhat different $T_m$ values against N-RAS and one pair of antisense oligonucleotides against APC and one pair of antisense oligonucleotides against BCR were examined. Various DNA masses were used in the PCRs. The only inhibitory effect was seen with an oligonucleotide against N-RAS with a high Tm, and then only after 33 PCR cycles.

FIG. 7 is a graphical representation of the fluorescence detection using Sybr Green or a Taqman probe. Three experiments were performed studying the N-RAS, APC and BCR genes and comparing the 2-phase nested PCR to the conventional PCR using the outer primers only. PCRs were started with various amounts of DNA and the endpoint was measured either by a Taqman probe or by Sybr Green. With conventional PCR, the Ct values with Sybr Green were less than those with Taqman, indicating that some non-specific material is amplified in the conventional PCR and measured by Sybr Green. This difference between the 2 endpoints was not seen in the 2 phase nested system, indicating the absence f the non-specific amplification in this system.

DETAILED DESCRIPTION OF THE PREFERRED EMBODIMENT

The present invention is predicated, in part, on the determination that by using primers with unique melting temperatures, and an antisense molecule which enables inactivation of the outer primers, one can design a single tube nested PCR method which maintains a constant and optimal level of efficiency thereby facilitating a quantitative PCR readout rather than just a qualitative readout. More specifically, this development has enabled a degree of control and robustness not previously available in the context of a single tube nested PCR. The method of the present invention is useful in the context of any application which requires the analysis of a specific DNA region of interest, such as a specific gene.

Accordingly, one aspect of the present invention is directed to a method of amplifying a nucleic acid region of interest, said method comprising:

(i) contacting a nucleic acid sample with:
  (a) a first forward primer directed to said region of interest and a first reverse primer directed to said region of interest; and
  (b) a second forward primer directed to said region of interest wherein said second forward primer is directed to a nucleic acid sequence located 3' to the sequence to which said first forward primer is directed and which second forward primer has a $T_m$ lower than the $T_m$ of said first forward primer; and
  a second reverse primer directed to said region of interest wherein said second reverse primer is directed to a nucleic acid sequence located 5' to the sequence to which said first reverse primer is directed and which second reverse primer has a $T_m$ lower than the $T_m$ of said first reverse primer; and
  (c) one or more antisense oligonucleotides directed to said first primer, which antisense oligonucleotides have a $T_m$ lower than said first primer; and
  wherein the molecules of parts (b) and (c) can be added to the reaction before, during or after the amplification of step (ii) but before the amplification of step (iii).

(ii) amplifying the nucleic acid sample of step (i) at an annealing temperature which enables hybridization of said first primers but which does not enable hybridization of said second primers and said antisense oligonucleotides; and (iii) amplifying the nucleic acid sample of step (ii) at an annealing temperature which enables hybridization of said second primers and said antisense oligonucleotides.

Reference to a nucleic acid "region of interest" should be understood as a reference to any region of DNA or RNA which is sought to be amplified. This may be a gene, part of a gene or an intergenic region. To this end, reference to "gene" should be understood as a reference to a DNA molecule which codes for a protein product, whether that be a full length protein or a protein fragment. In terms of chromosomal DNA, the gene will include both intron and exon regions. However, to the extent that the DNA of interest is cDNA, such as might occur if the DNA of interest is vector DNA or reverse transcribed mRNA, there may not exist intron regions. Such DNA may nevertheless include 5' or 3' untranslated regions. Accordingly, reference to "gene" herein should be understood to encompass any form of DNA which codes for a protein or protein fragment including, for example, genomic DNA and cDNA. The subject nucleic acid region of interest may also be a non-coding portion of genomic DNA which is not known to be associated with any specific gene (such as the commonly termed "junk" DNA regions). It may be any region of genomic DNA produced by recombination, either between 2 regions of genomic DNA or 1 region of genomic DNA and a region of foreign DNA such as a virus or an introduced sequence. It may be a region of a partly or wholly synthetically or recombinantly generated nucleic acid molecule. The subject nucleic acid sequence of interest may also be a region of DNA which has been previously amplified by any nucleic acid amplification method, including polymerase chain reaction (PCR) (i.e. it has been generated by an amplification method).

The subject "nucleic acid" region may be DNA or RNA or derivative or analogue thereof. Where the region of interest is a DNA sequence which encodes a proteinaceous molecule it may take the form of genomic DNA, cDNA which has been generated from a mRNA transcript, or DNA generated by nucleic acid amplification. However where the subject DNA does not encode a protein, either genomic DNA or synthetically or recombinantly generated DNA may be the subject of analysis. As would be appreciated by the skilled person, both synthetically and recombinantly generated DNA may also encode all or part of a protein. However, if the subject method is directed to detecting a region of RNA, it would be appreciated that it will first be necessary to reverse transcribe the RNA to DNA, such as using RT-PCR. The subject RNA may be any form of RNA, such as mRNA, primary RNA transcript, ribosomal RNA, transfer RNA, micro RNA or the like. Preferably, said nucleic acid region of interest is a DNA region of interest. To this end, said DNA includes DNA generated by reverse transcription from RNA which is ultimately the subject of analysis, and DNA generated by a nucleic acid amplification method such as PCR.

Accordingly, in one embodiment of the present invention is directed to a method of amplifying a DNA region of interest, said method comprising:

(i) contacting a DNA sample with:
  (a) a first forward primer directed to said region of interest and a first reverse primer directed to said region of interest; and
  (b) a second forward primer directed to said region of interest wherein said second forward primer is directed to a nucleic acid sequence located 3' to the sequence to which said first forward primer is directed and which second forward primer has a $T_m$ lower than the $T_m$ of said first forward primer; and
  a second reverse primer directed to said region of interest wherein said second reverse primer is directed to a nucleic acid sequence located 5' to the sequence to which said first reverse primer is directed and which second reverse primer has a $T_m$ lower than the $T_m$ of said first reverse primer; and
  (c) one or more antisense oligonucleotides directed to said first primer, which antisense oligonucleotides have a $T_m$ lower than said first primer; and
  wherein the molecules of parts (b) and (c) can be added to the reaction before, during or after the amplification of step (ii) but before the amplification of step (iii).

(ii) amplifying the DNA sample of step (i) at an annealing temperature which enables hybridization of said first primers but which does not enable hybridization of said second primers and said antisense oligonucleotides; and (iii) amplifying the DNA sample of step (ii) at an annealing temperature which enables hybridization of said second primers and said antisense oligonucleotides.

Reference to "DNA" should be understood as a reference to deoxyribonucleic acid or derivative or analogue thereof. In this regard, it should be understood to encompass all forms of DNA, including cDNA and genomic DNA. The nucleic acid molecules of the present invention may be of any origin including naturally occurring (such as would be derived from a biological sample), recombinantly produced or synthetically produced.

Reference to "derivatives" should be understood to include reference to fragments, homologs or orthologs of said DNA from natural, synthetic or recombinant sources. "Functional derivatives" should be understood as derivatives which exhibit any one or more of the functional activities of DNA. The derivatives of said DNA sequences include fragments having particular regions of the DNA molecule fused to other proteinaceous or non-proteinaceous molecules. "Analogs" contemplated herein include, but are not limited to, modifications to the nucleotide or nucleic acid molecule such as modifications to its chemical makeup or overall conformation. This includes, for example, incorporation of novel or modified purine or pyrimidine bases or modification to the manner in which nucleotides or nucleic acid molecules interact with other nucleotides or nucleic acid molecules such as at the level of backbone formation or complementary base pair hybridisation. The biotinylation or other form of labelling of a nucleotide or nucleic acid molecules is an example of a "functional derivative" as herein defined.

Preferably, said DNA is a gene or gene fragment, a chromosomal gene translocation breakpoint or DNA produced by prior nucleic acid amplification, such as PCR. The DNA of interest may be chemically synthesised or may be derived from the DNA or RNA of any organism including, but not limited to, any animal, plant, bacterium or virus.

In classical PCR, the primers and reaction conditions are designed so that hybridization and extension of the forward and reverse primers occur at or close to maximum efficiency so that the number of amplicons approximately doubles with each cycle, resulting in efficient exponential amplification. An adequate concentration of primers is important in achieving optimal efficiency. Greater specificity of DNA amplification can be obtained if two or more sets of primers are used in successive reactions. In this way, the impact of any non-specific products amplified from non-target areas can be minimised by conducting a further amplification using primers whose binding sites are located internal to those of the first set. The specificity of all the primers is combined, usually leading to a single product. A nested PCR can be performed as a sequential series of separate reactions or it can be performed in a single reaction container. Although the appeal of a single tube nested PCR reaction is obvious, the approach has suffered from problems such as the inconsistency of efficiency between different rounds of amplification, this leading to significant limitations where it has been desired to obtain a quantitative result. In order to effect amplification from different primer sets in a sequential order, many of the prior art methods have largely focussed on the method of lowering the concentration of the outer primers and having a high annealing temperature for the first phase and a lower temperature for the second phase. However, the efficiency of the amplification has differed significantly as between the different primer sets, thereby limiting the utility of this method.

Without limiting the present invention to any one theory or mode of action, it has been determined that the action of an antisense oligonucleotide directed to the outer primer, subsequent to amplification with the outer primer set, can effectively enable impairment of amplification via the outer forward primer. Hybridization of the antisense oligonucleotide to the outer primer will result in a decrease in concentration of free outer primer which in turn will lead to inefficiency of hybridization of that primer to the DNA target template. Hybridization is subject to a number of variables. The strength and extent of hybridization of the antisense oligonucleotide to the primer will depend on the Tm of the oligonucleotide which in turn will depend on its sequence and length, the presence of any mismatches or modifications which either decrease or increase hybridisation, the concentration of the oligonucleotide and the annealing temperature and time. Except for an antisense oligonucleotide for which the most 3' base of the antisense oligonucleotide hybridizes to the most 5' base of the primer, hybridization of the antisense oligonucleotide will result in it extending in the 3' direction. This will produce a longer antisense oligonucleotide with a higher Tm which will hybridize more strongly during subsequent cycles.

Appreciation of these various factors influencing hybridization will help those skilled in the art to design a single-tube nested PCR involving one or more antisense oligonucleotide primers such that hybridization of an antisense oligonucleotide to a primer is minimal or absent during the initial higher-temperature phase of the PCR but occurs during the subsequent lower-temperature phase. Those skilled in the art will also appreciate that during the high-temperature phase the outer primers are present at a high functional concentration and thus PCR amplification during this phase is at optimal efficiency whereas during the lower-temperature phase the outer primers are present at a much lower free concentration but the inner primers are present at a constant high concentration so that amplification can continue at optimal efficiency. During the lower-temperature phase amplification, once an amplicon has been initiated by an inner primer all subsequent amplicons "descendant" from it and generated during subsequent cycles will only be generated by the inner primers. Thus during this phase, amplification with each cycle will progressively transfer from being initiated by the outer primers to being initiated by the inner primers.

Reference to "primer" and "antisense oligonucleotide" should be understood as a reference to any molecule comprising a sequence of nucleotides, or functional derivatives or analogues thereof, the function of which includes hybridization to a region of a nucleic acid molecule of interest (the DNA of interest also being referred to as a "target DNA") and the amplification of the DNA sequence 5' to that region. It should be understood that the primer or antisense oligonucleotide may comprise non-nucleic acid components. For example, the primer or antisense oligonucleotide may also comprise a non-nucleic acid tag such as a fluorescent or enzymatic tag or some other non-nucleic acid component which facilitates the use of the molecule as a probe or which otherwise facilitates its detection or immobilisation. The primer or antisense oligonucleotide may also comprise additional nucleic acid components. In another example, the primer or antisense oligonucleotide may be a protein nucleic acid which comprises a peptide backbone exhibiting nucleic acid side chains. Preferably, said oligonucleotide primer is a DNA primer.

Reference to "forward primer" should be understood as a reference to a primer which amplifies the target DNA in the DNA sample of interest and in the PCR by hybridising to the antisense strand of the target DNA.

Reference to "reverse primer" should be understood as a reference to a primer which amplifies the target DNA in the DNA sample of interest and in the PCR by hybridising to the sense strand of the target DNA.

As detailed hereinbefore, a nested PCR is predicated on the use of two or more sets of forward and reverse primers which are directed to hybridising to progressively more internal sequences within the DNA region of interest. In the context of the present invention, reference to the "first" forward and reverse primer should be understood as a reference to the primers which hybridize at the outermost positions of the DNA region of interest. The "second" forward and reverse primers should be understood as a reference to internal primers. That is, these second primers are designed to hybridize to a sequence which is downstream of the first forward primer and upstream of the first reverse primer, respectively. It is within the skill of the person in the art to design at what intervals along the DNA region of interest these primers will hybridise. It should be understood that reference herein to a "third" forward and reverse primer set is a reference to a still more internal primer set which is designed to hybridize to a sequence which is downstream of the second forward primer and upstream of the second reverse primer, respectively.

The antisense oligonucleotide of the present invention is designed to hybridize to the specified forward primer. Accordingly, by "directed to" is meant that the antisense oligonucleotide hybridizes to a region of the subject primer. The antisense oligonucleotide may, therefore, hybridize across only part of the primer or it may hybridize across the full length of the primer. It should be understood that although this oligonucleotide is referred to as an "antisense" oligonucleotide, the use of this terminology is intended to indicate that the nucleotide sequence of this oligonucleotide is designed to enable the oligonucleotide to hybridize to the subject primer. It should also be understood that in terms of the nomenclature used in this specification to describe the antisense oligonucleotide, the end of the oligonucleotide which hybridizes to the 3' end of the primer is referred to as the 5' end of the oligonucleotide while the other end is the 3' end of the oligonucleotide.

Without limiting the present invention to any one theory or mode of action, the reaction of the present invention may be designed to use either one, or more than one, type of antisense oligonucleotide. Where more than one type of antisense oligonucleotide is used, these oligonucleotides may be designed to hybridize to different regions of the outer primer. It should also be understood that the antisense oligonucleotides which are utilised may be directed towards only the forward primer or only the reverse primer. In another alternative, the reaction may be designed to use both antisense oligonucleotides directed to the forward primer and antisense oligonucleotides directed to the reverse primer.

Also without limiting the present invention to any one theory or mode of action, the reaction of the present invention may be designed to use a semi-nested rather than a nested reaction. In this case, either a second forward or a second reverse primer is not used and antisense oligonucleotides directed to the single forward or single reverse primer that remains are not present.

The antisense oligonucleotide of the present invention may take the form of a simple antisense oligonucleotide or it may comprise additional functional or structural features which enhance or otherwise render still more effective its role of inhibiting ongoing amplification by the forward primers. These features may include, but are not limited to:

(i) 5' Tag on the Antisense Oligonucleotide.

This is an additional mechanism for inhibiting amplification by the outer primers and is based on designing the antisense oligonucleotide to hybridize to the 3' end of the forward or reverse primer and locating an oligonucleotide tag at the 5' end of the oligonucleotide (also herein interchangeably referred to as an oligonucleotide extension).

The effect of this oligonucleotide tag is illustrated in FIG. 2. When the primer hybridizes to the tagged antisense oligonucleotide, the primer extends in the 3' direction. Following dissociation of this duplex, and in the same or subsequent PCR cycles, the extended primer may hybridize to the complementary template strand. For efficient extension along the template, the sequence of the primer extension must be complementary to that sequence of the template strand which hybridizes to the extension, and for this to be the case the sequence of the oligonucleotide tag must be the same as that sequence of the template strand which hybridizes to the extension. Conversely, if the sequence of the oligonucleotide tag differs from that sequence of the template strand which hybridizes to the extension, further extension and amplification will not take place ie. the primer will have been inactivated. As a consequence, during the PCR at the permissive temperature, there occurs progressive inactivation of outer primer molecules with increasing cycle number and this phenomenon synergises with the direct inhibitory effect produced by hybridization of the antisense oligonucleotide to the outer primer. Those skilled in the art will appreciate that the essential property of the tag is to act as a template for 3' extension of the forward and/or reverse primer such that the extended primer is unable to act during subsequent PCR cycles; that this can be achieved by comprising the 5' antisense oligonucleotide tag of either normal nucleotides or modified nucleotides, such as either iso-deoxycytosine or iso-deoxyguanine (the complementary nucleotide must be present in the reaction); that the greater the difference between the sequence of the oligonucleotide tag and the sequence of the template strand which would hybridize to the extension, the greater the degree of primer inactivation, and that particularly efficient inactivation is produced by making the sequence of the oligonucleotide tag exactly complementary to that sequence of the template strand which would hybridize to the extension.

(ii) Inhibiting 3' Extension of the Antisense Oligonucleotide

The antisense oligonucleotide may be designed such that it can be prevented from undergoing 3' extension when it hybridizes to the primer. When an antisense oligonucleotide molecule hybridizes to a primer molecule at other than the 5' end of the primer, it will undergo 3' extension until it does reach the 5' end. Without limiting the present invention in any way, during subsequent PCR cycles, extended oligonucleotide molecules, which have an increased Tm, will exert a greater inhibitory effect on amplification by the outer primers, owing both to greater hybridization lowering the concentration of free primer and to greater hybridization leading to greater inactivation as a result of 3' primer extension along an oligonucleotide tag. This enhanced inhibitory effect of the 3' extended oligonucleotide may on occasion be counter-productive if it is so great as to lead to some inhibition of amplification during the high-temperature phase of the PCR. For this reason, prevention of 3' extension of the antisense oligonucleotide may be desirable.

Those skilled in the art will appreciate that 3' extension of the antisense oligonucleotide may be prevented by a number of different modifications of the 3' end. These include, but are not limited to:

locating a tag on the 3' end which results in a mismatch of the tag to the primer; or locating on the 3' end a molecule such as dideoxythymidine, iso-deoxycytosine or iso-deoxyguanine which does not allow extension; or phosphorylating the 3' end.

The results shown in FIGS. 1 and 3-6 used a mismatch tag of three nucleotides. Those skilled in the art will also appreciate that by using a mixture of oligonucleotides, either unmodified or modified at the 3' end, it will be possible to control the degree to which 3' extension of the antisense oligonucleotide occurs.

Accordingly, one embodiment of the present invention is directed to a method of amplifying a DNA region of interest, said method comprising:

(i) contacting a DNA sample with:
 (a) a first forward primer directed to said region of interest and a first reverse primer directed to said region of interest; and
 (b) a second forward primer directed to said region of interest wherein said second forward primer is directed to a nucleic acid sequence located 3' to the sequence to which said first forward primer is directed and which second forward primer has a $T_m$ lower than the $T_m$ of said first forward primer; and
 a second reverse primer directed to said region of interest wherein said second reverse primer is directed to a nucleic acid sequence located 5' to the sequence to which said first reverse primer is directed and which second reverse primer has a $T_m$ lower than the $T_m$ of said first reverse primer; and
 (c) one or more antisense oligonucleotides directed to said first primer, which antisense oligonucleotides have a $T_m$ lower than said first primers and one of which antisense oligonucleotide hybridizes to the 3' end of the primer and comprises a 5' nucleic acid tag sequence, the complementary nucleotide sequence of which tag is mismatched relative to the nucleotide sequence of the DNA region adjacent to the 5' end of the hybridization site of said primer wherein the molecules of parts (b) and (c) can be added to the reaction before, during or after the amplification of step (ii) but before the amplification of step (iii);

(ii) amplifying the DNA sample of step (i) at an annealing temperature which enables hybridization of said first primers but which does not enable hybridization of said second primers and said antisense oligonucleotides; and (iii) amplifying the DNA sample of step (ii) at an annealing temperature which enables hybridization of said second primers and said antisense oligonucleotides.

In another embodiment the present invention is directed to a method of amplifying a DNA region of interest, said method comprising:

(i) contacting a DNA sample with:
 (a) a first forward primer directed to said region of interest and a first reverse primer directed to said region of interest; and
 (b) a second forward primer directed to said region of interest wherein said second forward primer is directed to a nucleic acid sequence located 3' to the sequence to which said first forward primer is directed and which second forward primer has a $T_m$ lower than the $T_m$ of said first forward primer; and
 a second reverse primer directed to said region of interest wherein said second reverse primer is directed to a nucleic acid sequence located 5' to the sequence to which said first reverse primer is directed and which second reverse primer has a $T_m$ lower than the $T_m$ of said first reverse primer; and
 (c) one or more antisense oligonucleotides directed to said first primer, which antisense oligonucleotides have a $T_m$ lower than said first primers and one or more of which antisense oligonucleotides comprises a 3' end which cannot undergo normal extension wherein the molecules of parts (b) and (c) can be added to the reaction before, during or after the amplification of step (ii) but before the amplification of step (iii);

(ii) amplifying the DNA sample of step (i) at an annealing temperature which enables hybridization of said first primers but which does not enable hybridization of said second primers and said antisense oligonucleotides; and (iii) amplifying the DNA sample of step (ii) at an annealing temperature which enables hybridization of said second primers and said antisense oligonucleotides.

In still another embodiment, the present invention is directed to a method of amplifying a DNA region of interest, said method comprising:

(i) contacting a DNA sample with:
 (a) a first forward primer directed to said region of interest and a first reverse primer directed to said region of interest; and
 (b) a second forward primer directed to said region of interest wherein said second forward primer is directed to a nucleic acid sequence located 3' to the sequence to which said first forward primer is directed and which second forward primer has a $T_m$ lower than the $T_m$ of said first forward primer; and
 a second reverse primer directed to said region of interest wherein said second reverse primer is directed to a nucleic acid sequence located 5' to the sequence to which said first reverse primer is directed and which second reverse primer has a $T_m$ lower than the $T_m$ of said first reverse primer; and
 (c) one or more antisense oligonucleotides directed to said first primer, which antisense oligonucleotides have a $T_m$ lower than said first primers and which antisense oligonucleotides comprise:
  a 5' nucleic acid tag sequence on the antisense oligonucleotide which hybridizes to the 3' end of the primer, the complementary nucleotide sequence of which tag is mismatched relative to the nucleotide sequence of the DNA region adjacent to the 5' end of the hybridization site of said primer; and
  a 3' end which cannot undergo normal extension wherein the molecules of parts (b) and (c) can be added to the reaction before, during or after the amplification of step (ii) but before the amplification of step (iii);

(ii) amplifying the DNA sample of step (i) at an annealing temperature which enables hybridization of said first primers but which does not enable hybridization of said second primers and said antisense oligonucleotides; and (iii) amplifying the DNA sample of step (ii) at an annealing temperature which enables hybridization of said second primers and said antisense oligonucleotides.

Reference to "oligonucleotide tag" should be understood as a reference to a nucleotide sequence which is linked to the antisense oligonucleotide of the present invention. In one embodiment, the tag is 1-10 bases in length, preferably 2-5 bases in length and more preferably 2-3 bases in length.

The subject tag is designed such that the nucleotide sequence which is complementary to the sequence of the tag is "mismatched" relative to the nucleotide sequence of the DNA region 5' of the hybridization site of the 3' end of the primer. By "mismatched" is meant that the sequence of the tag is such that subsequently to hybridization of the primer to the antisense oligonucleotide and the extension of the primer along the tag, only the section of the extended primer which corresponds to the original primer will be able to hybridize to the DNA region of interest and the extended section will be of a sequence which does not facilitate its hybridization to the DNA region of interest. In this way, any further extension of this primer during amplification is inhibited since the 3' end of this primer cannot hybridize to the DNA region of interest. Accordingly, when the primer hybridizes to the antisense oligonucleotide, the primer extends in the 3' direction and produces a terminal sequence which prevents efficient extension in the 3' direction when the primer modified in this way subsequently hybridizes to its amplicon template.

The method of the present invention therefore enables an initial amplification off the outermost primers to initially proceed efficiently as the dominant amplification reaction. However, since it is sought to conclude this amplification and to proceed with amplification off the internal second primer set, effecting the hybridization of the antisense oligonucleotide and extension of the first forward primer along the tag region of the antisense oligonucleotide results in the generation of primers which are effectively blocked from undergoing any further extension in the context of the DNA region of interest. Together with the changes to the annealing temperature conditions, the ongoing unwanted amplification of the outer primers is minimised and the amplification of the inner primers can proceed under conditions which facilitate efficient amplification.

It should be understood that one may design the reaction to use antisense molecules directed to either the forward primer or the reverse primer or to both the forward and the reverse primers.

The design and synthesis of primers and antisense oligonucleotides suitable for use in the present invention would be well known to those of skill in the art. The Tm values of the primers and oligonucleotides would be largely determined by the annealing temperature which is desired for the various phases of the PCR. For example, for the experiments shown in FIGS. 1 and 3-6, an annealing temperature of 58° C. was desired for the second phase, owing to the use of a Taqman probe and in order to minimise non-specificity. It was empirically found that inner primers with Tm values of 58-66° C. and antisense oligonucleotides with Tm values of 48-52° C. would operate satisfactorily at this temperature but would lose effect at temperatures above 68-70° C. The annealing temperature of the first phase was therefore settled on as 72° C. This design for a single tube nested PCR appeared robust, as it worked well for the 4 genes investigated. Those skilled in the art would be able to modify the protocol if a lower annealing temperature were to be desired for the second phase or if a third phase was to be performed using an even lower temperature.

The subject primer may be of any suitable length which achieves the functional objective of having a particular annealing temperature. For example, the subject outer primer is 4 to 60 nucleotides in length, in another embodiment 10 to 50 in length, in yet another embodiment 15 to 45 in length, in still another embodiment 20 to 40 in length and in yet another embodiment 25 to 35 in length. In yet still another embodiment, primer is about 26, 27, 28, 29, 30, 31, 32, 33 or 34 nucleotides in length. The subject inner primer, which has a lower Tm and is generally shorter, is 4 to 50 nucleotides in length, in another embodiment 8 to 40 in length, in yet another embodiment 12 to 30 in length, in still another embodiment 13 to 30 in length, in yet another embodiment 14 to 25 in length and in yet still another embodiment 15, 16, 17, 18 19, 20, 21 or 22 nucleotides in length.

The primers of the present invention are designed to exhibit melting temperatures ($T_m$) different to one another, with the antisense oligonucleotide exhibiting yet still another $T_m$. Without limiting the present invention in any way, it is the combination of unique melting temperatures and the use of the antisense oligonucleotides which enables good amplification efficiency, in particular good efficiency of amplification, to be maintained from one amplification phase to the next. More specifically, the outermost primers are designed with the highest $T_m$. This enables the first phase amplification to be performed at a high annealing temperature and minimises non-specific annealing and amplification. In particular, annealing and amplification of the antisense oligonucleotide and the internal primers is not facilitated since these molecules exhibit lower $T_m$ values.

Those skilled in the art will readily be able to determine the ranges of annealing temperatures over which said first primers, said second primers and said antisense oligonucleotides hybridize and exert their actions either efficiently or inefficiently. Accordingly, the design of reaction conditions, for example determination of the "annealing temperature which enables hybridization of said first primers but which does not enable hybridization of said second primers and said antisense oligonucleotides", is a matter of routine procedure. The determination can be done directly by using one of the numerous qPCR instruments (such as the iQ real-time PCR instrument produced by BioRad) which provide a gradient of annealing temperature across a range of reaction wells so that individual PCRs can be performed at different annealing temperatures. The Ct values, and thus the annealing temperatures which enable or do not enable hybridization can be directly determined. Alternatively, the determination can be done indirectly by obtaining an estimated figure for the Tm of said first primers, said second primers and said antisense oligonucleotides by consulting one of the number of websites e.g., the world wide web address located at promega.com/biomath/calc11.htm, and the world wide web address located at idtdna.com/analyzer/Applications/OligoAnalyzer, which use a base-stacking algorithm to estimate the Tm. The results of experimentation in our laboratory indicate that the said first and second primers amplify efficiently at annealing temperatures below approximately their respective estimated Tm values plus 5° C.; that said second primers produce no significant amplification above approximately the respective estimated Tm values plus 7° C.; and that the said antisense oligonucleotides show measurable inhibition of amplification of the said first primers at annealing temperatures below approximately the estimated Tm of the oligonucleotide plus 10° C. Those skilled in the art will also appreciate that step (ii) can be conveniently performed at any annealing temperature in the range between the highest temperature which enables efficient amplification by said first primers and the lowest temperature at which said inner primers show no measurable amplification and said antisense oligonucleotides show no measurable inhibition and that step (iii) can be conveniently performed at any annealing temperature at which there is efficient amplification by said second primers and measurable inhibition by said antisense oligonucleotides.

It should also be understood that the amplification of step (ii) can be designed to not enable hybridization of the second primers and the antisense oligonucleotide by virtue of any suitable technique, such as, because the selected annealing temperature is greater than their respective $T_m$ values or simply because the second primers and the antisense oligonucleotides have not been added to the reaction mixture at the time that the amplification of step (ii) occurs.

In one example, the first set of outer primers are designed to exhibit a $T_m$ of 65-75° C. while the second set of inner primers are designed to exhibit a $T_m$ of approximately 10° C. lower, that is 55-65° C. If a third set of inner primers is utilised, these would be designed with a still lower $T_m$, such as 45-55° C. with the antisense oligonucleotide directed to the second forward primer exhibiting the lowest $T_m$. Accordingly, the subject melting temperatures of the different primers can be designed to exhibit differences of 5-15° C., first primer exhibits a $T_m$ of 70-75° C. while said second primer exhibits a $T_m$ of 58° C.-62° C. and said antisense oligonucleotide exhibits a $T_m$ of 48-52° C.

According to this embodiment there is provided a method of amplifying a DNA region of interest, said method comprising:
(i) contacting a DNA sample with:
(a) a first forward primer directed to said region of interest and a first reverse primer directed to said region of interest; and
(b) a second forward primer directed to said region of interest wherein said second forward primer is directed to a nucleic acid sequence located 3' to the sequence to which said first forward primer is directed and which second forward primer has a $T_m$ which is 5, 6, 7, 8, 9, 10, 11, 12, 13, 14, 15, 16, 17, 18, 19 or 20° C. lower than the $T_m$ of said first forward primer; and
a second reverse primer directed to said region of interest wherein said second reverse primer is directed to a nucleic acid sequence located 5' to the sequence to which said first reverse primer is directed and which second reverse primer has a $T_m$ which is 5, 6, 7, 8, 9, 10, 11, 12, 13, 14, 15, 16, 17, 18, 19 or 20° C. lower than the $T_m$ of said first reverse primer; and
(c) one or more antisense oligonucleotides directed to said first primer, which antisense oligonucleotides have a $T_m$ which is 10, 11, 12, 13, 14, 15, 16, 17, 18, 19, 20, 21, 22, 23, 24, 25, 26, 27, 28, 29 or 30° C. lower than said first primers and which antisense oligonucleotides comprise:
a 5' nucleic acid tag sequence on the antisense oligonucleotide which hybridizes to the 3' end of the primer, the complementary nucleotide sequence of which tag is mismatched relative to the nucleotide sequence of the DNA region adjacent to the 5' end of the hybridization site of said primer; and
a 3' end which cannot undergo normal extension
wherein the molecules of parts (b) and (c) can be added to the reaction before, during or after the amplification of step (ii) but before the amplification of step (iii); and
(ii) amplifying the DNA sample of step (i) at an annealing temperature which enables hybridization of said first primers but which does not enable hybridization of said second primers and said antisense oligonucleotides; and
(iii) amplifying the DNA sample of step (ii) at an annealing temperature which enables hybridization of said second primers and said antisense oligonucleotides.

In another embodiment, said first primers exhibit a $T_m$ of 65-75° C., preferably 69-73° C., said second primers exhibit a $T_m$ of 55-65° C., preferably 59-63° C., and said antisense oligonucleotide exhibits a $T_m$ of 45-55° C., preferably 49-52° C.

It should be understood that the primers, oligonucleotides and tags of the present invention should not be limited to the specific structure exemplified herein (being a linear, single-stranded molecule) but may extend to any suitable structural configuration which achieves the functional objectives detailed herein. For example, the primer may be designed to comprise a 5' sequence which itself can act as an antisense oligonucleotide to the sequence of the primer at the 3' end, forming a stem-loop structure, with or without a 5' tag, during the lower-temperature phase of the PCR; in this case a separate antisense oligonucleotide may not be required. Other examples can include:

a primer which consists of two or more hybridising sequences separated by one or more non-hybridising regions;

an antisense oligonucleotide which consists of two or more hybridising sequences separated by one or more non-hybridising or weakly hybridising regions, each such region comprising one or more non-hybridising or weakly hybridising bases or linkers;

an antisense oligonucleotide which is formed during the course of the PCR by ligation of two or more smaller antisense oligonucleotides.

Under some circumstances it may be desirable to perform a three-phase nested amplification. The principles and various modifications encompassed in the hereinbefore described embodiments may be used by those with skill in the art in order to design such an amplification.

Accordingly, another aspect of the present invention is directed to a method of amplifying a DNA region of interest, said method comprising:
(i) contacting a DNA sample with:
(a) a first forward primer directed to said region of interest and a first reverse primer directed to said region of interest; and
(b) a second forward primer directed to said region of interest wherein said second forward primer is directed to a nucleic acid sequence located 3' to the sequence to which said first forward primer is directed and which second forward primer has a $T_m$ lower than the $T_m$ of said first forward primer; and
a second reverse primer directed to said region of interest wherein said second reverse primer is directed to a nucleic acid sequence located 5' to the sequence to which said first reverse primer is directed and which second reverse primer has a $T_m$ lower than the $T_m$ of said first reverse primer; and
(c) a third forward primer directed to said region of interest wherein said third forward primer is directed to a DNA sequence located 3' to the sequence to which said second forward primer is directed and said third forward primer has a $T_m$ lower than the $T_m$ of said second forward primer; and
a third reverse primer directed to said region of interest wherein said third reverse primer is directed to a DNA sequence located 5' to the sequence to which said second reverse primer is directed and wherein said third reverse primer has a $T_m$ value lower than the $T_m$ values of said second reverse primer; and
(d) one or more antisense oligonucleotides directed to said first primer, which antisense oligonucleotides have a $T_m$ lower than said first primers and one or more antisense oligonucleotides directed to the said second primer, each of which antisense oligonucleotides has a $T_m$ lower than said second primers
wherein the molecules of parts (b), (c) and (d) can be added to the reaction before, during or after the amplification of step (ii) but before the amplification of step (iii);
(ii) amplifying the DNA sample of step (i) at an annealing temperature which enables hybridization of said first primers but which does not enable hybridization of said second primers and third primers and said antisense oligonucleotides; and
(iii) amplifying the DNA sample of step (ii) at an annealing temperature which enables hybridization of said second primers and said antisense oligonucleotides directed to said first primers but which does not enable hybridization of said third primers and said antisense oligonucleotides directed to said second primers;
(iv) amplifying the DNA sample of step (iii) at an annealing temperature which enables hybridization of said third primers and antisense oligonucleotides directed to the said second primers.

In one embodiment, the subject antisense oligonucleotides comprise:
a 5' nucleic acid tag sequence on the antisense oligonucleotide which hybridizes to the 3' end of the primer, the complementary nucleotide sequence of which tag is mismatched relative to the nucleotide sequence of the DNA region adjacent to the 5' end of the hybridization site of said primer; and a 3' end which cannot undergo normal extension An example of conditions which might be used in such an embodiment would be: the Tm values of the first forward and reverse primers to be 70-72° C., those of the second forward and reverse primers to be 58-62° C., and those of the third forward and reverse primers to be 42-50° C., and; the Tm values of the antisense oligonucleotides directed towards either or both of the first forward and reverse primers to be 48-52° C., and those of the antisense oligonucleotides directed towards either or both of the second forward and reverse primers to be 30-45° C. Using similar principles, one skilled in the art might be able to design a single tube nested PCR comprised of 4 phases which utilized 4 pairs of primers and 3 pairs of antisense oligonucleotides.

Facilitating the interaction of the primer and antisense oligonucleotide with the target DNA may be performed by any suitable method. Those methods will be known to those skilled in the art. To this end, it should be understood that the antisense oligonucleotide and/or the inner primers can be incorporated into the reaction tube at any suitable time point. While incorporation is generally prior to the commencement of the initial amplification cycles, that is together with the forward and reverse outer primers, incorporation of one or more may be performed subsequently to the initial amplification cycles with the outer primers. In either case, the antisense oligonucleotides exert their full effect only after the temperature of the reaction has been dropped to allow amplification by the second primer set. The mode of incorporation of the antisense oligonucleotide and/or the inner primers will depend on how the skilled person is seeking to perform the amplification reaction but, in general, for ease of use and avoidance of contamination, it is usually desirable to be able to perform the entire reaction in a single tube. Nevertheless, any other method of achieving the steps of the invention can be used.

The method of the present invention is preferably performed as a two phase reaction. The annealing temperature for phase one ensures that only the first outer primer set hybridize to any extent and not the antisense oligonucleotides or the second or third primer sets. The annealing temperature for phase two, however, is chosen to enable hybridization of the second primer set and antisense oligonucleotide directed to the first primer set. The appropriate number of cycles to be performed for each phase can be determined by the person of skill in the art. For example, 15-30 cycles can be typically used for the first phase and 10-40 cycles for the second phase. Rather than an abrupt decrease in annealing temperature at the commencement of the second phase of the PCR, the annealing temperature may be progressively decreased so that there is a gradual transition between the two phases.

Methods for achieving primer directed amplification are also very well known to those of skill in the art. In a preferred method, said amplification is polymerase chain reaction.

Reference to a "sample" should be understood as a reference to either a biological or a non-biological sample. Examples of non-biological samples includes, for example, the nucleic acid products of synthetically produced nucleic acid populations. Reference to a "biological sample" should be understood as a reference to any sample of biological material derived from an animal, plant or microorganism (including cultures of microorganisms) such as, but not limited to, cellular material, blood, mucus, faeces, urine, tissue biopsy specimens, fluid which has been introduced into the body of an animal and subsequently removed (such as, for example, the saline solution extracted from the lung following lung lavage or the solution retrieved from an enema wash), plant material or plant propagation material such as seeds or flowers or a microorganism colony. The biological sample which is tested according to the method of the present invention may be tested directly or may require some form of treatment prior to testing. For example, a biopsy sample may require homogenisation prior to testing. Further, to the extent that the biological sample is not in liquid form, it may require the addition of a reagent, such as a buffer, to mobilise the sample.

To the extent that the target DNA is present in a biological sample, the biological sample may be directly tested or else all or some of the nucleic acid material present in the biological sample may be isolated prior to testing. It is within the scope of the present invention for the target nucleic acid molecule to be pre-treated prior to testing, for example inactivation of live virus or being run on a gel. It should also be understood that the biological sample may be freshly harvested or it may have been stored (for example by freezing) prior to testing or otherwise treated prior to testing (such as by undergoing culturing).

Reference to "contacting" the sample with the primer or antisense oligonucleotide should be understood as a reference to facilitating the mixing of the primer with the sample such that interaction (for example, hybridisation) can occur. Means of achieving this objective would be well known to those of skill in the art.

The choice of what type of sample is most suitable for testing in accordance with the method disclosed herein will be dependent on the nature of the situation, such as the nature of the condition being monitored. For example, in a preferred embodiment a neoplastic condition is the subject of analysis. If the neoplastic condition is a leukaemia, a blood sample, lymph fluid sample or bone marrow aspirate would likely provide a suitable testing sample. Where the neoplastic condition is a lymphoma, a lymph node biopsy or a blood or marrow sample would likely provide a suitable source of tissue for testing. Consideration would also be required as to whether one is monitoring the original source of the neoplastic cells or whether the presence of metastases or other forms of spreading of the neoplasia from the point of origin is to be monitored. In this regard, it may be desirable to harvest and test a number of different samples from any one mammal. Choosing an appropriate sample for any given detection scenario would fall within the skills of the person of ordinary skill in the art.

The term "mammal" to the extent that it is used herein includes humans, primates, livestock animals (e.g. horses, cattle, sheep, pigs, donkeys), laboratory test animals (e.g. mice, rats, rabbits, guinea pigs), companion animals (eg dogs, cats) and captive wild animals (eg. kangaroos, deer, foxes). Preferably, the mammal is a human or a laboratory test animal. Even more preferably the mammal is a human.

Although the method of the present invention has been designed such that it is performed as a two phase amplification distinguished by a shift in annealing temperature, this should not be understood as a limitation in terms of whether any additional steps are sought to be incorporated by the skilled person, such as the provision of an efficient means of amplifying a nucleic acid region of interest. The method is useful in a range of applications including, but not limited to, the diagnosis and/or monitoring of disease conditions which are characterised by specific gene sequences, the characterisation or analysis of gene regions of interest and all the detection and quantification of bacteria, viruses or other actual or potentially pathogenic organisms, the study of forensic or archival DNA samples or the study of any samples in which non-specificity in the PCR is a problem.

The present invention is further described by reference to the following non-limiting examples.

Example 1

Consensus Criteria for Design of 2 Phase Nested Single Tube PCR Basic Cycling Conditions

| 96° C. - 2 min | 1x | Initial Taq activation |
| 94° C. - 15 sec | 15x | Phase I |
| 72° C. - 30 sec | | [outer primers amplify] |
| 72° C. - 30 sec | | |
| 58° C. - 5 min | 1x | Inactivation |
| 94° C. - 15 sec | 40x | Phase II |
| 58° C. - 90 sec | | [inner primers take |
| 72° C. - 60 sec | | over] |

Outer primers: 100 ng
Inner primers: 200 ng
Antisense oligonucleotide: same molarity as outer primers The annealing temperature of 72° C. for phase 1 is chosen to ensure that neither the antisense oligonucleotide nor the inner primers hybridize to any extent during this phase. The annealing temperature of 58° C. for phase 2 is chosen to enable annealing and hydrolysis of the Taqman probe and annealing of the inner primers. Although 15 cycles have generally been used for phase 1, experimentation has indicated that up to 30 cycles can be used, since an antisense oligonucleotide with a Tm of 50° C. does not cause measurable inhibition for at least 35 cycles at 72° C.

Target Tm Values

Use Promega base-stacking model, 2.5 mM magnesium, 2×dNTPs, 1:1 oligo ratio & assume 100 ng/PCR of outer primers and inner primers.

Outer primers: >=72° C.
Inner primers; 60-61° C.
Antisense oligonucleotide: 50° C. The Tm is calculated using the core base sequence and ignoring any 5' or 3' modifications. The system as described is fairly robust and will tolerate +/−2° C. in the Tm or a 2-fold variation in the molar ratio between the antisense oligonucleotide and the inner primer.

[Control Experiments

Outer primers: A gradient of annealing temperature is should be performed to ensure that these primers amplify efficiently at 72° C. When this has been established, experiments should be performed to ensure that neither the antisense oligonucleotides nor the inner primers inhibit amplification by the outer primers when the annealing temperature is maintained at 72° C.

Inner primers: A gradient of annealing temperature should be performed to ensure that these primers amplify efficiently at up to 62° C. and that above this temperature amplification efficiency decreases. When this has been established, experiments should be performed to ensure that the inner primers do not cause any amplification during phase 1.

Antisense oligonucleotides: Experiments should be performed to demonstrate the inhibitory effect of these oligonucleotides during phase 2. The approximate criterion that we have used is that when the amount of DNA in the PCR results in a Ct of approximately 23 with the complete 2 phase system, omission of the inner primers from the reaction will result in an increase in the Ct of at least 5 units.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Cheng et al., 1994, Effective amplification of long targets from cloned inserts and human genomic DNA. *Proc Natl Acad Sci.* 91:5695-5699

Ching J et al, 2006, Closed-system multi-stage nucleic acid amplification reactions United States Patent Application 20060177844

Du Breuil Lastrucci, et al 2007 Nested PCR employing degradable primers U.S. Pat. No. 7,273,730

Erlich H A, et al 1994 Methods for nucleic acid amplification U.S. Pat. No. 5,314,809

Grosz R et al 1994 Method for amplification of targeted segments of nucleic acid using nested polymerase chain reaction U.S. Pat. No. 5,340,728

Kemp D J et al, 1990, Simplified colorimetric analysis of polymerase chain reactions: detection of HIV sequences in AIDS *Gene,* 94: 223-228

Sambrook and Russel, 2001, *Molecular Cloning: A Laboratory Manual,* 3$^{rd}$ Ed. Cold Spring Harbor, N.W.: Cold Spring Harbor Laboratory Press. Chapter 8: In vitro Amplification of DNA by the Polymerase Chain Reaction.

Xu Dingbang Xie 2008 Single tube in situ nested polymerase chain reaction method and its use Publication CN1858219

Yourno J, 1996 Method and apparatus for nested polymerase chain reaction (PCR) with single closed reaction tubes U.S. Pat. No. 5,556,773

What is claimed is:

1. A method of amplifying a nucleic acid region of interest, said method comprising:
   (i) contacting a nucleic acid sample with:
      (a) a first forward primer directed to said region of interest and a first reverse primer directed to said region of interest; and
      (b) a second forward primer directed to said region of interest wherein said second forward primer is directed to a nucleic acid sequence located 3' to the sequence to which said first forward primer is directed and which second forward primer has a $T_m$ lower than the $T_m$ of said first forward primer; and
      a second reverse primer directed to said region of interest wherein said second reverse primer is directed to a nucleic acid sequence located 5' to the sequence to which said first reverse primer is directed and which second reverse primer has a $T_m$ lower than the $T_m$ of said first reverse primer; and
      (c) at least one antisense oligonucleotide directed to said first forward primer, said first reverse primer, or each of said first forward primer and said first reverse primer,
      wherein each antisense oligonucleotide has a $T_m$ lower than said first primers, and
      wherein each antisense oligonucleotide comprises a 5' nucleic acid tag sequence, the complementary nucleotide sequence of which tag is mismatched relative to the nucleotide sequence of the nucleic acid region adjacent to the 5' end of the hybridization site of said first primer to which the antisense oligonucleotide is directed, and wherein each antisense oligonucleotide hybridizes to the 3' end of the first forward primer or the 3' end of the first reverse primer; and (ii) amplifying the nucleic acid sample of step (i) at an annealing temperature which enables hybridization of said first primers but which does not enable hybridization of said second primers and said antisense oligonucleotides; and (iii) amplifying the nucleic acid sample of step (ii) at an annealing temperature which enables hybridization of said second primers and said antisense oligonucleotides;

wherein the molecules of parts (b) and (c) can be added to the reaction before, during or after the amplification of step (ii) but before the amplification of step (iii).

2. A method of amplifying a nucleic acid region of interest, said method comprising:
(i) contacting a DNA sample with:
(a) a first forward primer directed to said region of interest and a first reverse primer directed to said region of interest; and
(b) a second forward primer directed to said region of interest wherein said second primer is directed to a nucleic acid sequence located 3' to the sequence to which said first forward primer is directed and which second forward primer has a $T_m$ lower than the $T_m$ of said first forward primer; and
a second reverse primer directed to said region of interest wherein said second reverse primer is directed to a nucleic acid sequence located 5' to the sequence to which said first reverse primer is directed and which second reverse primer has a $T_m$ lower than the $T_m$ of said first reverse primer; and
(c) a third forward primer directed to said region of interest wherein said third forward primer is directed to a DNA sequence located 3' to the sequence to which said second forward primer is directed and said third forward primer has a $T_m$ lower than the $T_m$ of said second forward primer; and
a third reverse primer directed to said region of interest wherein said third reverse primer is directed to a DNA sequence located 5' to the sequence to which said second reverse primer is directed and wherein said third reverse primer has a $T_m$ value lower than the $T_m$ value of said second reverse primer; and
(d) at least one antisense oligonucleotide directed to said first forward primer, said first reverse primer, or each of said first forward and said first reverse primers, which antisense oligonucleotides have a $T_m$ lower than said first primers, and at least one antisense oligonucleotide directed to said second forward primer, said second reverse primer, or each of said second forward primer and said second reverse primer, each of which antisense oligonucleotides has a $T_m$ lower than said second primers and wherein each of said antisense oligonucleotides hybridizes to the 3' end of the primer to which it is directed and comprises a 5' nucleic acid tag sequence, the complementary nucleotide sequence of which tag is mismatched relative to the nucleotide sequence of the DNA region adjacent to the 5' end of the hybridization site of said primer to which the antisense oligonucleotide is directed;

(ii) amplifying the DNA sample of step (i) at an annealing temperature which enables hybridization of said first primers but which does not enable hybridization of said second primers and third primers and said antisense oligonucleotides;

(iii) amplifying the DNA sample of step (ii) at an annealing temperature which enables hybridization of said second primers and said antisense oligonucleotides directed to said first primers but which does not enable hybridization of said third primers and said antisense oligonucleotides directed to said second primers; and (iv) amplifying the DNA sample of step (iii) at an annealing temperature which enables hybridization of said third primers and said antisense oligonucleotides directed to said second primers;

wherein the molecules of parts (b), (c) and (d) can be added to the reaction before, during or after the amplification of step (ii) but before the amplification of step (iii).

3. The method of claim 1 wherein said nucleic acid is DNA.

4. The method of claim 3 wherein one or more of said antisense oligonucleotides comprises a 3' end which cannot undergo extension.

5. The method of claim 1 or 2 wherein said antisense oligonucleotides comprise:
a 3' end which cannot undergo extension.

6. The method of claim 5 wherein said 5' nucleic acid sequence tag is 1-10 bases in length.

7. The method of claim 6 wherein said 5' nucleic acid sequence tag is 2, 3, 4 or 5 bases in length.

8. The method of claim 7 wherein said 5' nucleic acid sequence tag is 2 or 3 bases in length.

9. The method of claim 3 wherein said first forward primer and said first reverse primer are each 10-50 nucleotides in length and said second forward primer and said second reverse primer are each 8-40 nucleotides in length.

10. The method of claim 9 wherein said first forward primer and said first reverse primer are each 15-45 nucleotides in length and said second forward primer and said second reverse primer are each 12-30 nucleotides in length.

11. The method of claim 10 wherein said first forward primer and said first reverse primer are each 20, 21, 22, 23, 24, 25, 26, 27, 28, 29, 30, 31, 32, 33, 34, 35, 36, 37, 38, 39 or 40 nucleotides in length.

12. The method of claim 10 wherein said second forward primer and said second reverse primer are each 13, 14, 15, 16, 17, 18, 19, 20, 21, 22, 23, 24, 25, 26, 27, 28, 29 or 30 nucleotides in length.

13. The method of claim 10 wherein said first forward primer and said first reverse primer are each 26, 27, 28, 29, 30, 31, 32, 33 or 34 nucleotides in length and said second forward primer and said second reverse primer are each 15, 16, 17, 18, 19, 20, 21 or 22 nucleotides in length.

14. The method of claim 3 wherein said second forward primer and said second reverse primer exhibit a $T_m$ of 5° C.-20° C. lower than the $T_m$ of said first forward primer and said first reverse primer, and said antisense oligonucleotide exhibits a $T_m$ of 5° C. to 20° C. lower than the $T_m$ of said second forward primer and said second reverse primer.

15. The method of claim 2 wherein said third forward primer and said third reverse primer exhibit a $T_m$ 5-20° C. lower than the $T_m$ of said second forward primer and said second reverse primer.

16. The method of claim 14 wherein said second forward primer and said second reverse primer exhibit a $T_m$ of 7° C., 8° C., 9° C., 10° C., 11° C., 12° C., 13° C., 14° C. or 15° C. lower than the $T_m$ of said first forward primer and said first reverse primer, and said antisense oligonucleotide exhibits a $T_m$ of 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C. or 30° C. lower than the $T_m$ of said first forward primer and said first reverse primer.

17. The method of claim 14 wherein said first forward primer and said first reverse primer exhibit a $T_m$ of 65° C.-75° C., said second forward primer and said second reverse primer exhibit a $T_m$ of 55° C.-65° C., and said antisense oligonucleotide exhibits a $T_m$ of 45° C.-55° C.

18. The method of claim 17 wherein said first forward primer and said first reverse primer exhibit a $T_m$ of 69-75° C., said second forward primer and said second reverse primer exhibit a $T_m$ of 59° C.-63° C., and said antisense oligonucleotide exhibits a $T_m$ of 49° C.-52° C.

19. The method of claim 15 wherein the $T_m$ of said first forward primer and said first reverse primer is 70° C.-72° C., the $T_m$ of said second forward primer and said second reverse primer is 58° C.-62° C., the $T_m$ of said third forward primer and said third reverse primer is 42° C.-50° C., and the $T_m$ of said antisense oligonucleotides is 30° C.-45° C.

\* \* \* \* \*